United States Patent
e Silva et al.

(10) Patent No.: US 7,259,294 B2
(45) Date of Patent: Aug. 21, 2007

(54) GTP BINDING STRESS-RELATED PROTEINS AND METHODS OF USE IN PLANTS

(75) Inventors: Oswaldo da Costa e Silva, Apex, NC (US); Hans J. Bohnert, Tucson, AZ (US); Nocha van Thielen, Cary, NC (US); Ruoying Chen, Apex, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 394 days.

(21) Appl. No.: 10/688,481

(22) Filed: Oct. 17, 2003

(65) Prior Publication Data

US 2004/0194163 A1 Sep. 30, 2004

Related U.S. Application Data

(62) Division of application No. 09/828,310, filed on Apr. 6, 2001, now Pat. No. 6,689,939.

(60) Provisional application No. 60/196,001, filed on Apr. 7, 2000.

(51) Int. Cl.
 *C12N 15/82* (2006.01)
 *C12N 15/29* (2006.01)
 *A01H 5/00* (2006.01)
 *A01H 5/10* (2006.01)

(52) U.S. Cl. .................. 800/289; 800/298; 536/23.6; 435/419

(58) Field of Classification Search ................ 435/419, 435/468, 320.1; 800/298, 289; 536/23.6
See application file for complete search history.

(56) References Cited

FOREIGN PATENT DOCUMENTS

WO WO98/00545 6/1997

OTHER PUBLICATIONS

Doerks T. et al. Protein annotation: detective work for function prediction. Trends Genet. Jun. 1998;14(6):248-50.*
Broun P et al. Catalytic plasticity of fatty acid modification enzymes underlying chemical diversity of plant lipids. Science. Nov. 13, 1998;282(5392):1315-7.*
Hill M.A. et al Functional analysis of conserved histidines in ADP-glucose pyrophosphorylase from *Escherichia coli*. Biochem Biophys Res Commun. Mar. 17, 1998;244(2):573-7.*
Bolte, S. et al., "Characterization of a Small GTP-Binding Protein of the Rab 5 Family in *Mesembryanthemum crystallinum* with Increased Level of Expression During Early Salt Stress", *Plant Molecular Biology*, 42:923-936, 2000.

Gammie, A.E. et al., "*DNM1*, a Dynamin-related Gene, Participates in Endosomal Trafficking in Yeast", *J. Cell Biol.*, 130:553-566; 1995.
Gu, X and Desh, P.S.V., "Phragmoplastin, a Dynamin-Like Protein Associated with Cell Plate Formation in Plants", *The EMBO Journal*, 15:695-704, 1996.
Ishitani, M. et al., "Coordinate Transcriptional Induction of myo-inositol Metabolism During Environmental Stress", *The Plant Journal*, 9(4):537-548, 1996.
O'Mahony, P.J. and Oliver, M.J., "Characterization of a Desiccation-Responsive Small GTP-Binding Protein (Rab2) from the Desiccation-Tolerant Grass *Sporobolus stapfianus*", *Plant Molecular Biology*, 39:809-821, 1999.
Park, J.M. et al., "A Dynamin-Like Protein in *Arabidopsis thaliana* is Involved in Biogenesis of Thylakoid Membranes", *The Embo Journal*, 17:859-867, 1998.
Robinson, P.J. et al., "Dynamin GTPase Regulated by Protein Kinase C Phosphorylation in Nerve Terminals", *Nature*, 365:163-166, 1993.
Shinozaki, K. and Yamaguchi-Shinozaki, K., "Molecular Responses to Dehydration and Low Temperature: Differences and Cross-Talk Between Two Stress Signaling Pathways", *Current Opinion in Plant Biology*, 3:217-223, 2000.
Wurgler-Murphy, S. and Saito, H., "Two-Component Signal Transducers and MAPK Cascades", *Trends in Biochemical Sciences*, 22:172-176, 1997.
Jenna L. Hutton et al., "The *Physcomitrella patens* GPa1 homologue is located at protonemal cell junctions", 1998, Journal of Experimental Botany, XP-001040374, vol. 49, No. 324, pp. 1113-1118.
H. Sano et al., "Expression of the gene for a small GTP binding protein in transgenic tobacco elevates endogenous cytokinin levels, abnormally induces salicylic acid in response to wounding, and increases resistance to tobacco mosaic virus infection", 1994, Proc. Natl. Acad. Sci. USA, XP-002195725, vol. 91, pp. 10556-10560.
Jesse Machuka et al., "Sequence analysis of Expressed Sequence Tags from an ABA-Treated cDNA Library Identifies Stress Response Genes in the Moss *Physcomitrella patens*", 1999, Plant Cell Physiol., XP-000946663, pp. 373-387; and.
Ralf Reski, "Molecular genetics of *Physcomitrella*", 1999, Plant Cell Physiol., XP-000881434, pp. 301-309.

* cited by examiner

*Primary Examiner*—Cynthia Collins
(74) *Attorney, Agent, or Firm*—Elaine Sale; Mark Westhafer; Rouying Chen

(57) ABSTRACT

A transgenic plant transformed by a GTP Binding Stress-Related Protein (GBSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated GBSRPs, and isolated nucleic acid coding GBSRPs, and vectors and host cells containing the latter.

14 Claims, 10 Drawing Sheets

(9 of 10 Drawing Sheet(s) Filed in Color)

PpGBP-1

Wild Type

PpGBP-2

Wild Type

PpGBP-3

Wild Type

PpGBP-4

Wild Type

PpGBP-1

Wild Type

PpGBP-2

Wild Type

PpGBP-3

Wild Type

PpGBP-4

Wild Type

PpGBP-5

Wild Type

SEQUENCE LISTING

<160> NUMBER OF SEQ ID NOS: 50

<210> SEQ ID NO 1
<211> LENGTH: 805
<212> TYPE: DNA
<213> ORGANISM: Physcomitrella patens

```
<400> SEQUENCE: 1
tttttttttt ttgggggaac aatatttgga agatacactt tacttcataa ttcggaaggt      60
caaaaactgt ctagaaaacc aaaacgttcc cgattacatg cacatccagc aaaactctga     120
tcgttatcgt cgctcttaaa caccgagcta agttcctctt tcacaggaaa acaatcactt     180
gatgtactgg gtcatccact tgaaaccttc accgtacccc attttgcgca caatactgca     240
catgaaaacc tcaatgggcc gaatgttgct atctcccagg ttcaccgttc ctttaccagt     300
ggtcatggtc aacccaagtg tgaaccgcaa ctcgtcttca gaagaagcgt acgggatatc     360
aatcttgttt cccaggacga gcacaggaac ttgggacaga gaatcgtcgg agagaagaga     420
atcgagctct tcttttgact cagcaaatct ctccctgtct actgcgtcga cgagatacac     480
tatagcatcc accttagcat agtagtccct ccacacgcgt cgagcgattg tgtggccacc     540
cagatcgaat gctttgaact tcactctgtt gatactcaac tcctctgacg ttggatactg     600
cgttggttga tgttgcccca gtttctcatc cttgagcatg tgcagaagag tagtcttgcc     660
agcattgtcg agacccagaa acaggatttt ggcctccttc tgccacagcc ctatgctcgc     720
aagaaagccg taaaaccaat ctacaagaaa catggtacca gccttggtat ctacggaccc     780
gccccaattt tccacgacct cgtgc                                           805

<210> SEQ ID NO 2
<211> LENGTH: 671
<212> TYPE: DNA
<213> ORGANISM: Physcomitrella patens

<400> SEQUENCE: 2
gcaccaggcg ccgcctgcct cagctcttag ttctccgaat ttgacacttg tttcgtttgc      60
ttccttcttt ttttattttt tttatttttct tcttagtctt cttcctctct tgctcatccc    120
caatggctga gactttagtg ctgcgcggga ctttgaaggg tcattccaac tgggtgaccg     180
ccatcgcctg ccctctcgac aaccctgacc tcatcctctc gtcgtctcgc gacaagagca     240
tcatcgtctg gaccctcacc cgcgaggagg gcaactatgg tgtcgcccgc cgtaggctga     300
ccgggcacgc tcacttcgtg caggatgtgg tgatctcctc cgacggacag ttcgccctgt     360
cggggtcgtg ggacgggacc ttgcgttttgt gggatttgaa caccggaact accaccggc     420 ggttcatcgg tcacaccaag gatgtgctca gcgtggcttt ctccgttgat aacagacaga     480
ttgtgtcggg atcccgcgac aagacaatca agctgtggaa cactcttggt gagtgcaagt     540
acaccatcca ggacgtcgat gcccacactg ggtgggtgag ctgcgtccga ttctcccctg     600
tgactgctaa ccctatcatt gtgtccggtg ggtgggacaa ggttgtcaag gtgtggaacc     660
tgaccaactg c                                                         671

<210> SEQ ID NO 3
<211> LENGTH: 749
<212> TYPE: DNA
<213> ORGANISM: Physcomitrella patens

<400> SEQUENCE: 3
gtattccccc cgttgtttca agcttttgca aacctgaatc acatcacgtt gagtcttctg      60
ctgagtctca aagtagggga tccctccttt cctggcacac catgctttgc cttcttctcg     120
gagaccactc gactattgcc accatccacg tccactttat gttccaagta ctacaaaggg     180
gaagttctcc tgatcggatg ggcttgcctg aatcagaaac tcgtccctcc agttgtcaag     240
gttatcaaaa gacttcataa cattcacatc gtagacaaga acacaacatc tgcaccacga     300
```

```
taaaaggcga ctccaagact ctgaaaccgc tcttgcccag ctgtatccca aatctgcatc    360
gtaacaagtc tgtcttcaac ctgcacttcc ttagttagaa agtctgcccc aatagtggcc    420
ttatattgat tgctgaattt cttattaaca tactgattca tcaaagaagt ctttccaacc    480
ccgctatcac cgaggatgat aactttcaac aacgtcctct tgcgggccga catcgcagac    540
tgattctcca atctcctgct tccaattctt aaccctcaca actgccctgg ctccaaaatc    600
acgccttcct tcacgactcc ctccccggtc ccaagcagag cttctcgatg aaaattgttc    660
ttcgaaaacc gagatccgcg gctgtagtgc atcaaattct acaaggaaga gtgcgttctg    720
gtgccgagga atcgagcgta cactggtgc                                     749

<210> SEQ ID NO 4
<211> LENGTH: 815
<212> TYPE: DNA
<213> ORGANISM: Physcomitrella patens
<220> FEATURE:
<221> NAME/KEY: modified_base
<222> LOCATION: (782)
<223> OTHER INFORMATION: a, t, c, g, other or unknown

<400> SEQUENCE: 4
cggcaccaga aaatatacgc ggtgttcgac aatcaactgc cagctgcttt gaagaagctt     60
ccgttcgaca agcatctgtc tgggcagaat gtgcgaagga ttgtttcgga ggctgatggt    120
taccagcccc atcttatagc tccggagcaa ggttacaggc ggctaattga agttcgctg     180 caatttttca ggggcccagc ggaggcagta gtggatgcag taagtcactc tgttgcaacg    240
ataaatgaac agtaacgttt ctagattttc acgaattcaa tttttctcca tcaaggatat    300
tttctagtca cgacattctg catacttacc agtagcacag ggttcggctg attcgtgatt    360
gtgtgacaac ccaggtgcat ttcattctta gggacctggt gcgaaaatcg atcggagagt    420
gttcggtaag ggtctgagac tttggaattt ccttgcctgt aagaacgtgc tgggttacca    480
gcggaacctg tcacttgtga ccaccaagag tgctagctat atctttctag cttatgttaa    540
ttggtttaat gttttttagta cctcactgac ttaaaccgaa cttggaagcg agaataggaa    600
tgatgtgctt gatgtcaacc ttcattctca caggaactga agagatttcc atcactccaa    660
gcggagatgg tcaagcagcc attgagtcgt tagagaggat gaagatgaga gcagaagacc    720 cttttgaggcg gggacatgga atcacctacc tgacgggcaa ttttccgaag ctgcgaaaat    780
gnaaggtgaa ccgcgcgcag taagacgtac ggtac                              815

<210> SEQ ID NO 5
<211> LENGTH: 490
<212> TYPE: DNA
<213> ORGANISM: Physcomitrella patens

<400> SEQUENCE: 5
gcacgagtgc ttctgtagct cccgattcac ctgccttgca tagatcgtcg tccaccctca     60
accagattgg tgcacaatgg ccgcagacga cgagaagcaa gcacgggagg tggaggagac    120
aaccggatcg gaagctcctg cggaaggagc tgatgagcct accaaggctg gcgaggagga    180
ggacacaggt gctcaaatcg cgcctatcgt aacattacag gaagttgctg ttagcactgg    240
cgaagaggat gaagacgtgc tgattgatat gaaagctaag ctttaccgat tgacaagga     300 aggaacccag tggaaagagc ggggcgttgg ccaagttaag atattagagc ataagactac    360
cagaaaggtc cgattgctca tgcgacaaaa tcggaccctg aagatctgtg ctaatcacat    420
```

```
ggttacggca gctactcaac tgcaagagca cgctggtagt gataagtcat ggatatggca    480
tgcgcgagac                                                           490

<210> SEQ ID NO 6
<211> LENGTH: 667
<212> TYPE: DNA
<213> ORGANISM: Physcomitrella patens

<400> SEQUENCE: 6
atcccgggtc cgtagatacc aaggctggta ccatgtttct tgtagattgg ttttacggct     60
ttcttgcgag catagggctg tggcagaagg aggccaaaat cctgtttctg ggtctcgaca    120
atgctggcaa gactactctt ctgcacatgc tcaaggatga gaaactgggg caacatcaac    180
caacgcagta tccaacgtca gaggagttga gtatcaacag agtgaagttc aaagcattcg    240
atctgggtgg ccacacaatc gctcgacgcg tgtgggagga ctactatgct aaggtggatg    300
ctatagtgta tctcgtcgac gcagtagaca gggagagatt tgctgagtca agaaagagc    360 tcgattctct tctctccgac gattctctgt cccaagttcc tgtgctcgtc ctgggaaaca    420
agattgatat cccgtacgct tcttctgaag acgagttgcg gttcacactt gggttgacca    480
tgaccactgg taaaggaacg gtgaacctgg gagatagcaa cattcggccc attgaggttt    540
tcatgtgcag tattgtgcgc aaaatggggt acggtgaagg tttcaagtgg atgacccagt    600
acatcaagtg attgttttcc tgtgaaagag gaacttagct cggtgtttaa gagcgacgag    660
ttaacgc                                                              667

<210> SEQ ID NO 7
<211> LENGTH: 1045
<212> TYPE: DNA
<213> ORGANISM: Physcomitrella patens

<400> SEQUENCE: 7
atcccgggcc tctcttgctc atccccaatg gctgagactt tagtgctgcg cgggactttg     60
aaggttcatt ccaactgggt gaccgccatc gcctgccctc tcgacaaccc tgacctcatc    120
ctctcgtcgt ctcgcgacaa gagcatcatc gtctggaccc tcacccgcga ggagggcaac    180
tatggtgtcg cccgccgtag gctgaccggg cacgctcact tcgtgcagga tgtggtgatc    240
tcctccgacg gacagttcgc cctgtcgggg tcgtgggacg ggaccttgcg tttgtgggat    300
ttgaacaccg gaactaccac ccggcggttc atcggtcaca ccaaggatgt gctcagcgtg    360
gctttctccg ttgataacag acagattgtg tcgggatccc gcgacaagac aatcaagctg    420
tggaacactc ttggtgagtg caagtacacc atccaggacg tcgatgccca cactgggtgg    480
gtgagctgcg tccgattctc ccctgtgact gctaacccta tcattgtgtc cggtgggtgg    540
gacaaggttg tcaaggtgtg gaacctgacc aactgcaaga ttcgctccaa cttggttggc    600
cacaccggat atgtcaacac agtaactgta tcccctgatg gttcgttgtg cgccagcgga    660
ggtaaggatg gagtcgccat gttgtgggat ttgtctgagg gcaagaggct gtactcactg    720
gacgccggtg atatcatcca ctcccttttgc tttagcccca acagatactg gttgtgtgcc    780
gccacccaat cctgcatcaa gatctgggac ttggagagca agagcattgt cgatgagttg    840
cgccccgagt tcactttcgt cagtaagaag gcccagattc cttactgcgt cagcttgaac    900
tggagcgctg acgggagcac tcttttcagt ggttacactg atggccacat tagggtgtgg    960
gccgtcggaa gggcttaagc gtcttctcat ttacggggtc gcaatgcgga agtacggcgt   1020
tctctgatta gtgcctcgag ctcgc                                         1045
```

<210> SEQ ID NO 8
<211> LENGTH: 698
<212> TYPE: DNA
<213> ORGANISM: Physcomitrella patens

<400> SEQUENCE: 8

```
atcccgggca ggagattgga gaatcagtct gcgatgtcgg cccgcaagag gacgttgttg      60
aaagttatca tcctcggtga tagcggggtt ggaaagactt ctttgatgaa tcagtatgtt     120
aataagaaat tcagcaatca atataaggcc actattgggg cagactttct aactaaggaa     180
gtgcaggttg aagacagact tgttacgatg cagatttggg atacagctgg gcaagagcgg     240
tttcagagtc ttggagtcgc cttttatcgt ggtgcagatt gttgtgttct tgtctacgat     300
gtgaatgtta tgaagtcttt tgataacctt gacaactgga gggacgagtt tctgattcag     360
gcaagcccat ccgatcagga gaacttcccc tttgtagtac ttggaaataa agtggacgtg     420
gatggtggca atagtcgagt ggtctccgag aagaaggcca agcatggtg tgcagcgaaa      480
ggaggcatcc cctactttga gacatcagcc aaggaagact tcaacgtgga tgctgcattc     540
cagtgtattg ccaagaacgc attgaagaac gagacggagg aggaaattta cctgcctgat     600
acgatcgacg tgaacgccag caggccacag aaaacttccg gatgcgagtg ttaagagtag     660
cggagttgct gcgatgggaa atgccaggtc gagctcgc                             698
```

<210> SEQ ID NO 9
<211> LENGTH: 2119
<212> TYPE: DNA
<213> ORGANISM: Physcomitrella patens

<400> SEQUENCE: 9

```
atcccgggca cgcctccacc ctcttgggtc acatctcttt cttctctggt gggcgtcgca      60
cttctgcaac cgatcgccgg aagcctagat accgacattg gcggtaccag gcttgcggga     120
cttgggcgta cgaatactt gtaaatccaa ggggagattg caagatggat aatttgattg      180
ggcttgtgaa taggattcag agggcttgca ctgccctcgg tgaccatgga ggcgaaggtg     240
cagttgcaag tctctgggag gccttgcctt cggttgctgt cgttggtggg cagagttcgg     300
gaaagtcttc agtgctggaa agtatcgttg acgtgattt ctccctcgg ggttctggta       360
tcgttactag gcgtccgttg gttttgcaac tgcacaaaac tgatgaaggc acacaggagt     420
acgcagagtt tctccacatg cccaaaaagc ggtttactga ctttgctgct gtaaggaagg     480
agatctcaga cgagacggac cgaatgactg gacggggcaa gggaatttcg gttgtgccaa     540
ttcagcttag cgtttattcc cccaatgttg tgaatttgac tctcatcgat cttccgggac     600
ttacaaaaat tgctgttgat ggccaatccg acagcatcgt gcaagacatt gagaacatgg     660
tccggtcata tattgagaag caaaattcta tcattcttgc cgtgtctcca gcgaatcaag     720
atatcgccac ttcagatgct atgaagattg ctagagaagt ggatcctact ggagagagga     780
cttttgggt ccttaccaag ttggatctga tggacaaggg gacaaatgcc cttgatgtcc       840
ttgaaggacg ctcctaccgt ttacaacatc cgtgggtagg agttgtgaat cgttcccagc     900
aggcatcaa caaggaagtg aacatgatag cagcaagacg cagagagcga gaatactttg      960
caaccagtca agattacggt cacctggcca gcaagatggg ttctgaatat ttggggaaag    1020
tgctctccaa gcatttggaa gccgtgatca agtcccgtat tcctagcatc caggctatga    1080
ttaacaaaag tattgacgag atcgagatgg agctgaatca gatcggccgg cctcttgcaa    1140
```

-continued

```
atgatgcagg ggctcagctg tacactatcc tggaactttg tcgggccttc gatcgaatct    1200
tcaaggacca tctggatgga gcacgccccg gtggtgataa aatatacgcg gtgttcgaca    1260
atcaactgcc agctgctttg aagaagcttc cgttcgacaa gcatctgtct gggcagaatg    1320
tgcgaaggat tgtttcggag gctgatggtt accagcccca tcttatagct ccggagcaag    1380
gttacaggcg gctaattgaa agttcgctgc aattttttcaa gggcccagcg gaggcagtag    1440
tggatgcagt gcatttcatt cttagggacc tggtgcgaaa atcgatcgga gagtgttcgg    1500
aactgaagag atttccatca ctccaagcgg agattgctca agcagccatt gagtcgttag    1560
agaggatgag agatgagagc aagaagacca ctttgaggct ggtggacatg gaatccagct    1620
acctgaccgt ggacttttc gaaagctgc cgcaagagat tgagaagggt ggaaacgctg    1680
ctgccgcagc taacgaccgt tacacggata accacttgcg gcgcattggt tccaatgtgg    1740
cagcgtacgt tggcatggtt tgcgatcagc tgaggaactc tttgcccaaa gctgctgtcc    1800
actgtcaagt tcgagaagcg aagaggtcat tgatggacca cttttacact caaataggca    1860
agcgggaggg aaagcaattg tcagcgatgc tggatgagga ccctgctttg atggaacgga    1920
gagttcagct gtcaaagaga ctggagcttt acaaacaagc cagggacgag attgattctg    1980
ttgcctggaa gtagttgggg ggtcgtactt aatttatacc tatttcatta ctgaatgttg    2040
catttattca tagcagctct tttcccttgg agaacgataa ttacagttac atccaagccc    2100
tcaactccca ggagctcgc                                                 2119
```

<210> SEQ ID NO 10
<211> LENGTH: 883
<212> TYPE: DNA
<213> ORGANISM: Physcomitrella patens

<400> SEQUENCE: 10

```
atcccgggcg tccaccctca accagattgg tgcacaatgg ccgcagacga cgagaagcaa     60
gcacgggagg tggaggagac aaccggatcg gaagctcctg cggaaggagc tgatgagcct    120
accaaggctg cgcaggagga ggacacaggt gctcaaatcg cgcctatcgt aacattacag    180
gaagttgctg ttagcactgg cgaagaggat gaagacgtgc tgattgatat gaaagctaag    240
ctttaccgat ttgacaagga aggaacccag tggaaagagc ggggcgttgg ccaagttaag    300
atattagagc ataagactac cagaaaggtc cgattgctca tgcgacaaaa tcggaccctg    360
aagatctgtg ctaatcacat ggttacggca gctactcaac tgcaagagca cgctggtagt    420
gataagtcat ggatatggca tgcgcgagac tattcagacg gcgagttaaa ggaggagctt    480
ttctgcatgc gatttggcag tgttgaaagc gcccaaaagt ttaaagatgt ttatgaggct    540
gcccaggaga aggtgtctag caagacagag gagaaggacg aggaggctga tgcgactgca    600
gaccttttac aaaatttgaa agtggaacca aaaactgata aggtcgatgt tcctgaggaa    660
acgaatactg gaaccaaagc agcgtagatt ggacagtatg ggtgtgatca acatgtgctt    720
gggtcgttgg aaggtagtta tacgtggcac taaactggtt tcgagtgttg atgtttttaa    780
accctcgtcc agggtcggaa tttggaatgc ttctcctgaa gtgaaaaaag ttaatcgtgt    840
aaacctttat tagtgttaat aagtacgcca gttgcgagct cgc                     883
```

<210> SEQ ID NO 11
<211> LENGTH: 192
<212> TYPE: PRT
<213> ORGANISM: Physcomitrella patens

<400> SEQUENCE: 11

```
Met Phe Leu Val Asp Trp Phe Tyr Gly Phe Leu Ala Ser Ile Gly Leu
 1               5                  10                  15

Trp Gln Lys Glu Ala Lys Ile Leu Phe Leu Gly Leu Asp Asn Ala Gly
                 20                  25                  30

Lys Thr Thr Leu Leu His Met Leu Lys Asp Glu Lys Leu Gly Gln His
                 35                  40                  45

Gln Pro Thr Gln Tyr Pro Thr Ser Glu Glu Leu Ser Ile Asn Arg Val
         50                  55                  60

Lys Phe Lys Ala Phe Asp Leu Gly Gly His Thr Ile Ala Arg Arg Val
 65                  70                  75                  80

Trp Arg Asp Tyr Tyr Ala Lys Val Asp Ala Ile Val Tyr Leu Val Asp
                 85                  90                  95

Ala Val Asp Arg Glu Arg Phe Ala Glu Ser Lys Lys Glu Leu Asp Ser
                100                 105                 110

Leu Leu Ser Asp Asp Ser Leu Ser Gln Val Pro Val Leu Val Leu Gly
                115                 120                 125

Asn Lys Ile Asp Ile Pro Tyr Ala Ser Ser Glu Asp Glu Leu Arg Phe
130                 135                 140

Thr Leu Gly Leu Thr Met Thr Thr Gly Lys Gly Thr Val Asn Leu Gly
145                 150                 155                 160

Asp Ser Asn Ile Arg Pro Ile Glu Val Phe Met Cys Ser Ile Val Arg
                165                 170                 175

Lys Met Gly Tyr Gly Glu Gly Phe Lys Trp Met Thr Gln Tyr Ile Lys
                180                 185                 190

<210> SEQ ID NO 12
<211> LENGTH: 316
<212> TYPE: PRT
<213> ORGANISM: Physcomitrella patens

<400> SEQUENCE: 12

Met Ala Glu Thr Leu Val Leu Arg Gly Thr Leu Lys Gly His Ser Asn
 1               5                  10                  15

Trp Val Thr Ala Ile Ala Cys Pro Leu Asp Asn Pro Asp Leu Ile Leu
                 20                  25                  30

Ser Ser Ser Arg Asp Lys Ser Ile Ile Val Trp Thr Leu Thr Arg Glu
                 35                  40                  45

Glu Gly Asn Tyr Gly Val Ala Arg Arg Leu Thr Gly His Ala His
         50                  55                  60

Phe Val Gln Asp Val Val Ile Ser Ser Asp Gly Gln Phe Ala Leu Ser
 65                  70                  75                  80

Gly Ser Trp Asp Gly Thr Leu Arg Leu Trp Asp Leu Asn Thr Gly Thr
                 85                  90                  95

Thr Thr Arg Arg Phe Ile Gly His Thr Lys Asp Val Leu Ser Val Ala
                100                 105                 110

Phe Ser Val Asp Asn Arg Gln Ile Val Ser Gly Ser Arg Asp Lys Thr
                115                 120                 125

Ile Lys Leu Trp Asn Thr Leu Gly Glu Cys Lys Tyr Thr Ile Gln Asp
130                 135                 140

Val Asp Ala His Thr Gly Trp Val Ser Cys Val Arg Phe Ser Pro Val
145                 150                 155                 160

Thr Ala Asn Pro Ile Ile Val Ser Gly Gly Trp Asp Lys Val Val Lys
                165                 170                 175

Val Trp Asn Leu Thr Asn Cys Lys Ile Arg Ser Asn Leu Val Gly His
```

-continued

```
                180                 185                 190
Thr Gly Tyr Val Asn Thr Val Thr Val Ser Pro Asp Gly Ser Leu Cys
            195                 200                 205

Ala Ser Gly Gly Lys Asp Gly Val Ala Met Leu Trp Asp Leu Ser Glu
210                 215                 220

Gly Lys Arg Leu Tyr Ser Leu Asp Ala Gly Asp Ile Ile His Ser Leu
225                 230                 235                 240

Cys Phe Ser Pro Asn Arg Tyr Trp Leu Cys Ala Ala Thr Gln Ser Cys
                245                 250                 255

Ile Lys Ile Trp Asp Leu Glu Ser Lys Ser Ile Val Asp Glu Leu Arg
            260                 265                 270

Pro Glu Phe Thr Phe Val Ser Lys Lys Ala Gln Ile Pro Tyr Cys Val
            275                 280                 285

Ser Leu Asn Trp Ser Ala Asp Gly Ser Thr Leu Phe Ser Gly Tyr Thr
        290                 295                 300

Asp Gly His Ile Arg Val Trp Ala Val Gly Arg Ala
305                 310                 315
```

<210> SEQ ID NO 13
<211> LENGTH: 206
<212> TYPE: PRT
<213> ORGANISM: Physcomitrella patens

<400> SEQUENCE: 13

```
Met Ser Ala Arg Lys Arg Thr Leu Leu Lys Val Ile Ile Leu Gly Asp
1               5                   10                  15

Ser Gly Val Gly Lys Thr Ser Leu Met Asn Gln Tyr Val Asn Lys Lys
            20                  25                  30

Phe Ser Asn Gln Tyr Lys Ala Thr Ile Gly Ala Asp Phe Leu Thr Lys
        35                  40                  45

Glu Val Gln Val Glu Asp Arg Leu Val Thr Met Gln Ile Trp Asp Thr
    50                  55                  60

Ala Gly Gln Glu Arg Phe Gln Ser Leu Gly Val Ala Phe Tyr Arg Gly
65                  70                  75                  80

Ala Asp Cys Cys Val Leu Val Tyr Asp Val Asn Val Met Lys Ser Phe
                85                  90                  95

Asp Asn Leu Asp Asn Trp Arg Asp Glu Phe Leu Ile Gln Ala Ser Pro
            100                 105                 110

Ser Asp Gln Glu Asn Phe Pro Phe Val Val Leu Gly Asn Lys Val Asp
        115                 120                 125

Val Asp Gly Gly Asn Ser Arg Val Val Ser Glu Lys Lys Ala Lys Ala
    130                 135                 140

Trp Cys Ala Ala Lys Gly Gly Ile Pro Tyr Phe Glu Thr Ser Ala Lys
145                 150                 155                 160

Glu Asp Phe Asn Val Asp Ala Ala Phe Gln Cys Ile Ala Lys Asn Ala
                165                 170                 175

Leu Lys Asn Glu Thr Glu Glu Ile Tyr Leu Pro Asp Thr Ile Asp
            180                 185                 190

Val Asn Ala Ser Arg Pro Gln Lys Thr Ser Gly Cys Glu Cys
        195                 200                 205
```

<210> SEQ ID NO 14
<211> LENGTH: 609
<212> TYPE: PRT
<213> ORGANISM: Physcomitrella patens

<400> SEQUENCE: 14

```
Met Asp Asn Leu Ile Gly Leu Val Asn Arg Ile Gln Arg Ala Cys Thr
1               5                   10                  15

Ala Leu Gly Asp His Gly Gly Glu Gly Ala Val Ala Ser Leu Trp Glu
            20                  25                  30

Ala Leu Pro Ser Val Ala Val Gly Gly Gln Ser Ser Gly Lys Ser
        35                  40                  45

Ser Val Leu Glu Ser Ile Val Gly Arg Asp Phe Leu Pro Arg Gly Ser
    50                  55                  60

Gly Ile Val Thr Arg Arg Pro Leu Val Leu Gln Leu His Lys Thr Asp
65              70                  75                  80

Glu Gly Thr Gln Glu Tyr Ala Glu Phe Leu His Met Pro Lys Lys Arg
                85                  90                  95

Phe Thr Asp Phe Ala Ala Val Arg Lys Glu Ile Ser Asp Glu Thr Asp
            100                 105                 110

Arg Met Thr Gly Arg Gly Lys Gly Ile Ser Val Val Pro Ile Gln Leu
        115                 120                 125

Ser Val Tyr Ser Pro Asn Val Val Asn Leu Thr Leu Ile Asp Leu Pro
    130                 135                 140

Gly Leu Thr Lys Ile Ala Val Asp Gly Gln Ser Asp Ser Ile Val Gln
145             150                 155                 160

Asp Ile Glu Asn Met Val Arg Ser Tyr Ile Glu Lys Gln Asn Ser Ile
                165                 170                 175

Ile Leu Ala Val Ser Pro Ala Asn Gln Asp Ile Ala Thr Ser Asp Ala
            180                 185                 190

Met Lys Ile Ala Arg Glu Val Asp Pro Thr Gly Glu Arg Thr Phe Gly
        195                 200                 205

Val Leu Thr Lys Leu Asp Leu Met Asp Lys Gly Thr Asn Ala Leu Asp
    210                 215                 220

Val Leu Glu Gly Arg Ser Tyr Arg Leu Gln His Pro Trp Val Gly Val
225             230                 235                 240

Val Asn Arg Ser Gln Gln Asp Ile Asn Lys Glu Val Asn Met Ile Ala
                245                 250                 255

Ala Arg Arg Arg Glu Arg Glu Tyr Phe Ala Thr Ser Gln Asp Tyr Gly
            260                 265                 270

His Leu Ala Ser Lys Met Gly Ser Glu Tyr Leu Gly Lys Val Leu Ser
        275                 280                 285

Lys His Leu Glu Ala Val Ile Lys Ser Arg Ile Pro Ser Ile Gln Ala
    290                 295                 300

Met Ile Asn Lys Ser Ile Asp Glu Ile Glu Met Glu Leu Asn Gln Ile
305             310                 315                 320

Gly Arg Pro Leu Ala Asn Asp Ala Gly Ala Gln Leu Tyr Thr Ile Leu
                325                 330                 335

Glu Leu Cys Arg Ala Phe Asp Arg Ile Phe Lys Asp His Leu Asp Gly
            340                 345                 350

Ala Arg Pro Gly Gly Asp Lys Ile Tyr Ala Val Phe Asp Asn Gln Leu
        355                 360                 365

Pro Ala Ala Leu Lys Lys Leu Pro Phe Asp Lys His Leu Ser Gly Gln
    370                 375                 380

Asn Val Arg Arg Ile Val Ser Glu Ala Asp Gly Tyr Gln Pro His Leu
385             390                 395                 400

Ile Ala Pro Glu Gln Gly Tyr Arg Arg Leu Ile Glu Ser Ser Leu Gln
                405                 410                 415
```

```
Phe Phe Lys Gly Pro Ala Glu Ala Val Asp Ala Val His Phe Ile
            420                 425                 430

Leu Arg Asp Leu Val Arg Lys Ser Ile Gly Glu Cys Ser Glu Leu Lys
            435                 440                 445

Arg Phe Pro Ser Leu Gln Ala Glu Ile Ala Gln Ala Ile Glu Ser
            450                 455                 460

Leu Glu Arg Met Arg Asp Glu Ser Lys Lys Thr Thr Leu Arg Leu Val
465                 470                 475                 480

Asp Met Glu Ser Ser Tyr Leu Thr Val Asp Phe Phe Arg Lys Leu Pro
                    485                 490                 495

Gln Glu Ile Glu Lys Gly Gly Asn Ala Ala Ala Ala Asn Asp Arg
                500                 505                 510

Tyr Thr Asp Asn His Leu Arg Arg Ile Gly Ser Asn Val Ala Ala Tyr
            515                 520                 525

Val Gly Met Val Cys Asp Gln Leu Arg Asn Ser Leu Pro Lys Ala Ala
            530                 535                 540

Val His Cys Gln Val Arg Glu Ala Lys Arg Ser Leu Met Asp His Phe
545                 550                 555                 560

Tyr Thr Gln Ile Gly Lys Arg Glu Gly Lys Gln Leu Ser Ala Met Leu
                565                 570                 575

Asp Glu Asp Pro Ala Leu Met Glu Arg Arg Val Gln Leu Ser Lys Arg
                580                 585                 590

Leu Glu Leu Tyr Lys Gln Ala Arg Asp Glu Ile Asp Ser Val Ala Trp
            595                 600                 605

Lys

<210> SEQ ID NO 15
<211> LENGTH: 216
<212> TYPE: PRT
<213> ORGANISM: Physcomitrella patens

<400> SEQUENCE: 15

Met Ala Ala Asp Asp Glu Lys Gln Ala Arg Glu Val Glu Glu Thr Thr
1               5                   10                  15

Gly Ser Glu Ala Pro Ala Glu Gly Ala Asp Glu Pro Thr Lys Ala Gly
                20                  25                  30

Glu Glu Glu Asp Thr Gly Ala Gln Ile Ala Pro Ile Val Thr Leu Gln
            35                  40                  45

Glu Val Ala Val Ser Thr Gly Glu Glu Asp Val Leu Ile Asp
    50                  55                  60

Met Lys Ala Lys Leu Tyr Arg Phe Asp Lys Glu Gly Thr Gln Trp Lys
65                  70                  75                  80

Glu Arg Gly Val Gly Gln Val Lys Ile Leu Glu His Lys Thr Thr Arg
                85                  90                  95

Lys Val Arg Leu Leu Met Arg Gln Asn Arg Thr Leu Lys Ile Cys Ala
            100                 105                 110

Asn His Met Val Thr Ala Ala Thr Gln Leu Gln Glu His Ala Gly Ser
            115                 120                 125

Asp Lys Ser Trp Ile Trp His Ala Arg Asp Tyr Ser Asp Gly Glu Leu
        130                 135                 140

Lys Glu Glu Leu Phe Cys Met Arg Phe Gly Ser Val Glu Ser Ala Gln
145                 150                 155                 160

Lys Phe Lys Asp Val Tyr Glu Ala Ala Gln Glu Lys Val Ser Ser Lys
                165                 170                 175
```

Thr Glu Glu Lys Asp Glu Glu Ala Asp Ala Thr Ala Asp Leu Leu Gln
            180                 185                 190

Asn Leu Lys Val Glu Pro Lys Thr Asp Lys Val Asp Val Pro Glu Glu
        195                 200                 205

Thr Asn Thr Gly Thr Lys Ala Ala
    210                 215

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 16
caggaaacag ctatgacc                                                 18

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 17
ctaaagggaa caaaagctg                                                19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 18
tgtaaaacga cggccagt                                                 18

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19
tgccagcatt gtcgagaccc agaaa                                         25

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 20
atcccgggtc cgtagatacc aaggctggt                                     29

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 21
gcgttaactc gtcgctctta aacaccgagc taag              34

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 22
atcccgggcc tctcttgctc atccccaatg gctg              34

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 23
gcgagctcga ggcactaatc agagaacgcc gta               33

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 24
cacaactgcc ctggctccaa aatca                       25

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 25
atcccgggca ggagattgga gaatcagtct gc                32

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 26
gcgagctcga ccctggcatt tcccatcgca gcaa              34

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 27
tactgcatcc actactgcct ccgct                       25

<210> SEQ ID NO 28
<211> LENGTH: 33
<212> TYPE: DNA

```
<213> ORGANISM: Artificial Sequence
<220> FEATURE:
<223> OTHER INFORMATION: Description of Artificial Sequence: Primer

<400> SEQUENCE: 28
atcccgggca cgcctccacc ctcttgggtc aca                                33

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 29
gcgagctcct gggagttgag ggcttggatg taa                                33

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 30
tgtcctcctc ctcgccagcc ttggt                                         25

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 31
atcccgggcg tccaccctca accagattgg tgc                                33

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 32
gcgagctcgc aactggcgta cttattaaca cta                                33

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 33
gcgctgcaga tttcatttgg agaggacacg                                    30

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 34
cgcggccggc ctcagaagaa ctcgtcaaga aggcg                              35
```

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 35
gctgacacgc caagcctcgc tagtc                                         25

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 36
gcgttaactc gtcgctctta aacaccgagc taag                               34

<210> SEQ ID NO 37
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 37
gcgagctcga ggcactaatc agagaacgcc gta                                33

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 38
gcgagctcga ccctggcatt tcccatcgca gcaa                               34

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 39
gcgagctcct gggagttgag ggcttggatg taa                                33

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 40
gcgagctcgc aactggcgta cttattaaca cta                                33

<210> SEQ ID NO 41
<211> LENGTH: 29
<212> TYPE: DNA
<213> ORGANISM: Artificial Sequence
<220> FEATURE:

<223> OTHER INFORMATION: Description of Artificial Sequence: Primer

<400> SEQUENCE: 41
atcccgggtc cgtagatacc aaggctggt                              29

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 42
gcgttaactc gtcgctctta aacaccgagc taag                        34

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 43
atcccgggcc tctcttgctc atccccaatg gctg                        34

<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 44
gcgagctcga ggcactaatc agagaacgcc gta                         33

<210> SEQ ID NO 45
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 45
atcccgggca ggagattgga gaatcagtct gc                          32

<210> SEQ ID NO 46
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 46
gcgagctcga ccctggcatt tcccatcgca gcaa                        34

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 47
ggcacacagg agtacgcaga gtttc                                  25

```
-continued

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 48
cgctctctgc gtcttgctgc tatcatg                                          27

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 49
atcccgggcg tccaccctca accagattgg tgc                                   33

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 50
gcgagctcgc aactggcgta cttattaaca cta                                   33
```

GTP BINDING STRESS-RELATED PROTEINS AND METHODS OF USE IN PLANTS

CROSS REFERENCE TO RELATED APPLICATIONS

This application is a divisional application of U.S. Nonprovisional Patent application Ser. No. 09/828,310 filed Apr. 6, 2001, now U.S. Pat. No. 6,689,939 and claims the priority benefit of U.S. Provisional Application Ser. No. 60/196,001 filed Apr. 7, 2000, and the entire contents of both applications are hereby incorporated by reference.

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as rice, maize (corn) and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Continuous exposure to drought and high salt causes major alterations in the plant metabolism. These great changes in metabolism ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance in model, drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerance plants using biotechnological methods.

Therefore, what is needed is the identification of the genes and proteins involved in these multi-component processes leading to stress tolerance. Elucidating the function of genes expressed in stress tolerant plants will not only advance our understanding of plant adaptation and tolerance to environmental stresses, but also may provide important information for designing new strategies for crop improvement.

There are at least four different signal-transduction pathways leading to stress tolerance in the model plant *Arabidopsis thaliana*. These pathways are under the control of distinct transcription factors, protein kinases, protein phosphatases and other signal-transduction pathway components (Shinozaki et al. 2000 Curr. Op. Pl. Biol. 3:217–23). These proteins are prime targets for engineering stress tolerance since they could function as master switches; alterations in a single gene would lead to activation of an entire signal-transduction chain leading to stress tolerance.

Sensing of osmotic stress in bacteria as well as in plants is performed by a two-component system comprising a sensing protein and an effecting protein (Wurgler-Murphy S M and Saito S. 1997. Trends in Biochem. Sci. 22:172–6 and Shinozaki et al. 2000. Curr. Op. Pl. Biol. 3: 217–23). Mitogen-activated protein kinase-dependent signal transduction pathways are tightly involved in these processes. Another major component of these signal-transduction chains are GTP-binding proteins (G-proteins). Generally speaking, there are at least three classes of G-proteins: a) heterotrimeric (alpha, beta and gamma subunits), b) monomeric (small) proteins, and c) Dyanins. GTP-binding proteins are named as such because each must bind GTP in order to be active. The functions of GTP-binding proteins are varied as they range from directly transmitting an external signal (by being associated with a membrane-bound receptor), to participating in vesicle traffic, to importing proteins into sub-cellular compartments.

The participation of trimeric G-proteins in stress tolerance has not yet been directly demonstrated. However, since they are associated with membrane-bound receptors, they may be involved in transmitting the sensed stress signal leading to stress tolerance. Binding of the ligand to a receptor could conceivably cause the activation of the alpha subunit and thereby change the concentration of a low-molecular weight second messenger. Changes in the concentration of second messengers, like cAMP in animal systems, ultimately activate further components of the signal transduction pathway and second messengers such as inositol derivatives have been implicated in stress tolerance in plants (Ishitani et al. 1996 Pl Journal 9:537–48).

Monomeric/small G-proteins are also involved in many different cellular processes and have been implicated in vesicle traffic/transport, cell cycle and protein import into organelles. Several groups have identified small G-proteins, homologous to the Rab family of small G-proteins, as being induced upon desiccation treatments in plants (Bolte et al. 2000 Plant Mol. Biol. 42:923–36; O'Mahony and Oliver 1999 Plant Mol. Biol. 39:809–21). These researchers speculate that the small G-proteins could be involved in preservation of membrane integrity or re-structuring upon relief of stress. However, they have not produced transgenic plants with increased stress tolerance by over-expression of these small G-proteins.

Another class of G-proteins is the high-molecular weight G-proteins. Dynamins are a representative member of this class. There have been several homologs of high molecular weight G-proteins identified in a number of eukaryotic systems, including yeast, human, rat and mouse and in plant systems including *Arabidopsis thaliana, Nicotiana tabacum* and *Glycine max*. Although sequence and proposed functions of the different homologs are diverse, they all appear to function in protein trafficking, likely assisting in vesicle formation. The most thoroughly characterized Dynamin to date was isolated from rat and has been shown to bind to microtubules and participate in endocytosis while being regulated by phosphorylation (Robinson et al. 1993 Nature 365:163–166.). Additionally, plant Dynamin isolated from *Glycine max* was found to be localized across the whole width of the newly formed cell plate during cytokinesis, suggesting a role for the protein for depositing cell plate material via exocytic vesicles (Gu &Verma 1996. EMBO J. 15:695–704). The protein, ADL1, isolated from *Arabidopsis*, has been shown to be localized to the thylakoid membranes in sub-organellar fractionation of chloroplasts from leaves. Transgenic plants over-expressing a mutant form of this gene show a reduced number of chloroplasts and those existing chloroplasts had a reduced number of thylakoids and thylakoid membrane proteins. These data suggest a role for ADL1 in transport of protein needed for biogenesis of thylakoid membranes (Park et al. 1998 EMBO J. 17:859–867). One other such homologue, DNM1, found in *Saccharomyces cerevisiae* also participates in endocytosis, acting at a novel step before fusion with the late endosome (Gammie et al. 1995. J. Cell Biol. 130:553–566). Despite this research however, the participation of Dynamins in stress tolerance has not been demonstrated.

There is a need, therefore, to identify genes expressed in stress tolerant plants that have the capacity to confer stress resistance to its host plant and to other plant species. Newly generated stress tolerant plants will have many advantages, such as increasing the range that crop plants can be cultivated by, for example, decreasing the water requirements of a plant species.

SUMMARY OF THE INVENTION

This invention fulfills in part the need to identify new, unique GTP-binding proteins capable of conferring stress tolerance to plants upon over-expression. The present invention provides a transgenic plant cell transformed by a GTP Binding Stress-Related Protein (GBSRP) coding nucleic acid, wherein expression of the nucleic acid sequence in the plant cell results in increased tolerance to environmental stress as compared to a wild type variety of the plant cell. Namely, described herein are the G-proteins: 1) GTP Binding Protein-1 (GBP-1); 2) GTP Binding Protein-1 (GBP-2); 3) GTP B inding Protein-3 (GBP-3); 4) GTP Binding Protein-4 (GBP-4); and 5) GTP Binding Protein-5 (GBP-5), all from *Physcomitrella patens*.

The invention provides in some embodiments that the GBSRP and coding nucleic acid are that found in members of the genus *Physcomitrella*. In another preferred embodiment, the nucleic acid and protein are from a *Physcomitrella patens*. The invention provides that the environmental stress can be salinity, drought, temperature, metal, chemical, pathogenic and oxidative stresses, or combinations thereof. In preferred embodiments, the environmental stress can be drought or cold temperature.

The invention further provides a seed produced by a transgenic plant transformed by a GBSRP coding nucleic acid, wherein the plant is true breeding for increased tolerance to environmental stress as compared to a wild type variety of the plant. The invention further provides a seed produced by a transgenic plant expressing a GBSRP, wherein the plant is true breeding for increased tolerance to environmental stress as compared to a wild type variety of the plant.

The invention further provides an agricultural product produced by any of the below-described transgenic plants, plant parts or seeds. The invention further provides an isolated GBSRP as described below. The invention further provides an isolated GBSRP coding nucleic acid, wherein the GBSRP coding nucleic acid codes for a GBSRP as described below.

The invention further provides an isolated recombinant expression vector comprising a GBSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a GBSRP coding nucleic acid, wherein expression of the nucleic acid in the plant results in increased tolerance to environmental stress as compared to a wild type variety of the plant comprising: (a) transforming a plant cell with an expression vector comprising a GBSRP coding nucleic acid, and (b) generating from the plant cell a transgenic plant with an increased tolerance to environmental stress as compared to a wild type variety of the plant. In preferred embodiments, the GBSRP and GBSRP coding nucleic acid are as described below.

The present invention further provides a method of identifying a novel GBSRP, comprising (a) raising a specific antibody response to a GBSRP, or fragment thereof, as described below; (b) screening putative GBSRP material with the antibody, wherein specific binding of the antibody to the material indicates the presence of a potentially novel GBSRP; and (c) identifying from the bound material a novel GBSRP in comparison to known GBSRP. Alternatively, hybridization with nucleic acid probes as described below can be used to identify novel GBSRP nucleic acids.

The present invention also provides methods of modifying stress tolerance of a plant comprising, modifying the expression of a GBSRP in the plant, wherein the GBSRP is as described below. The invention provides that this method can be performed such that the stress tolerance is either increased or decreased. Preferably, stress tolerance is increased in a plant via increasing expression of a GBSRP.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

*Arabidopsis* lines. The transgenic lines display a tolerant phenotype. Individual transformant lines are shown.

Figure 1:
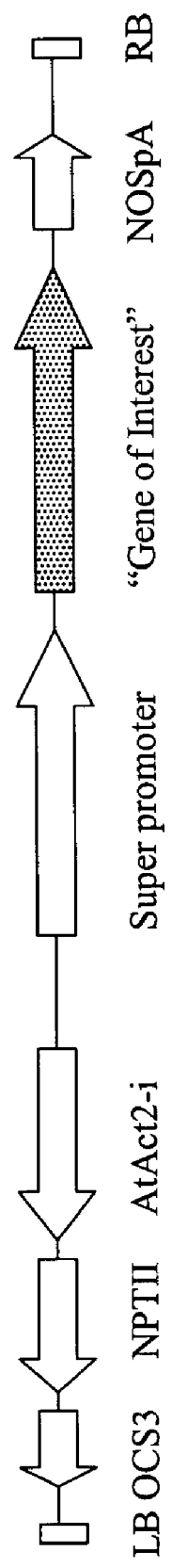
FIG. 1 shows a diagram of the plant expression vector pBPSSC022 containing the super promoter driving the expression of SEQ ID NOs: 6, 7, 8, 9 and 10 ("Desired Gene"). The components are: NPTII kanamycin resistance gene (Hajdukiewicz et al. 1994 Pl. Mol Biol. 25: 989–98), AtAct2-i promoter (An et al. 1996 Plant J. 10: 107–21), OCS3 terminator (Weigel et al. 2000 Pl. Physiol. 122: 1003–13).
Figure 2:
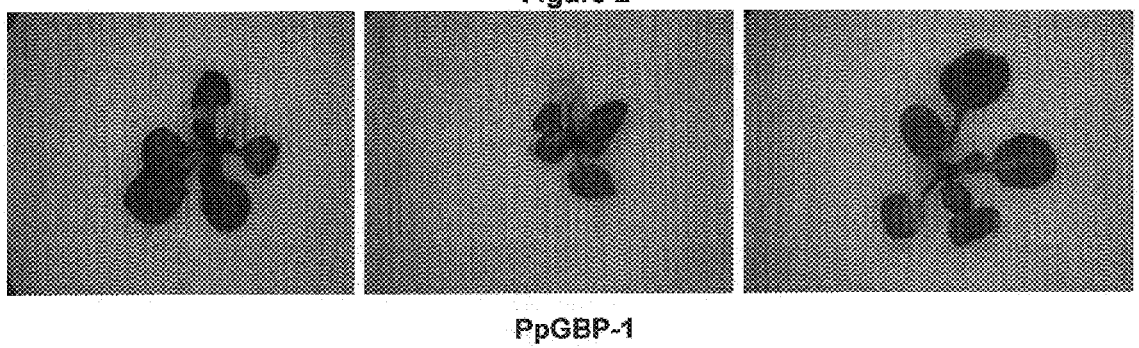
FIG. 2 show the results of a drought stress test with over-expressing PpGBP-1 transgenic plants and wild-type *Arabidopsis* lines. The transgenic lines display a tolerant phenotype. Individual transformant lines are shown.
Figure 2:
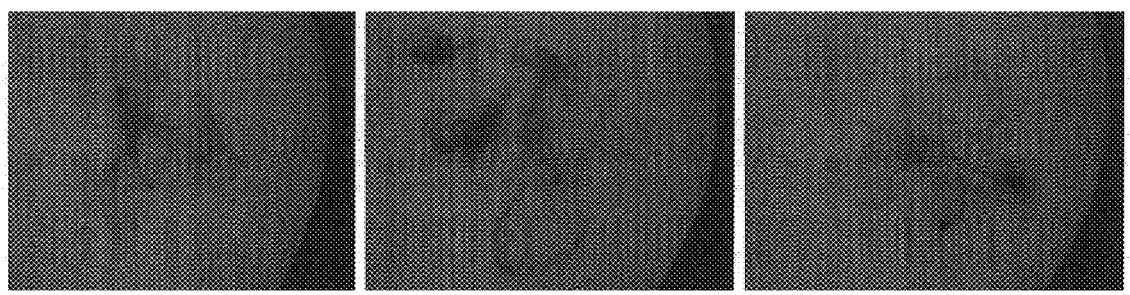
Figure 3:
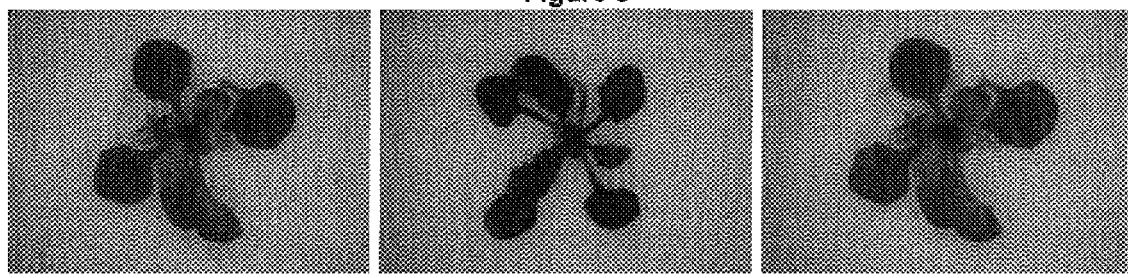
FIG. 3 show the results of a drought stress test with over-expressing PpGBP-2 transgenic plants and wild-type *Arabidopsis* lines. The transgenic lines display a tolerant phenotype. Individual transformant lines are shown.
Figure 3:
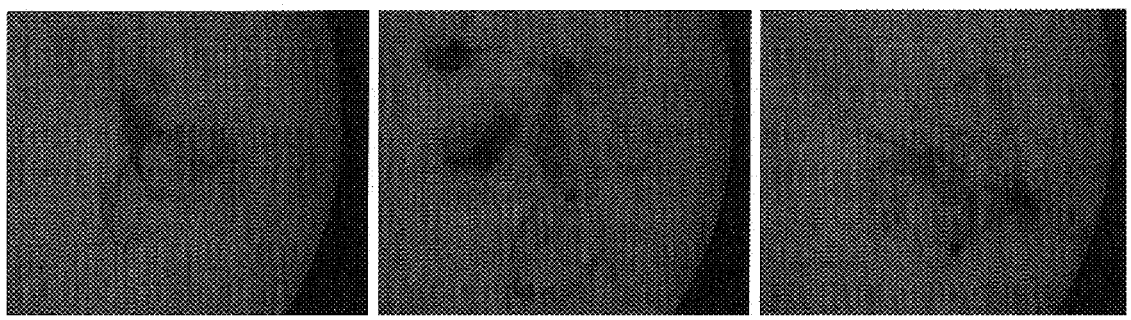
Figure 4:
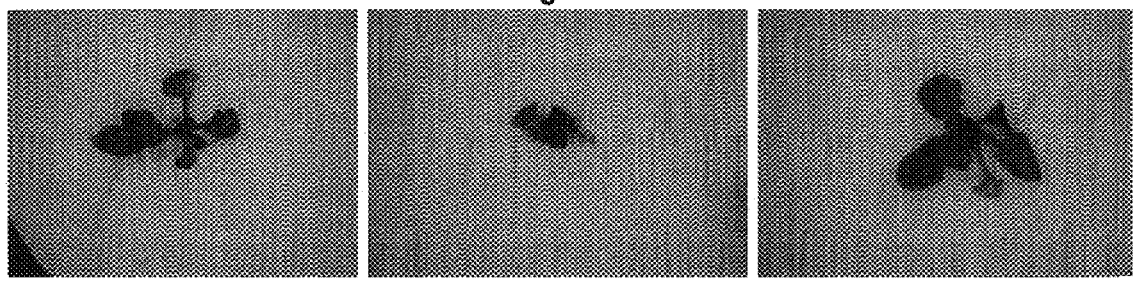
FIG. 4 show the results of a drought stress test with over-expressing PpGBP-3 transgenic plants and wild-type *Arabidopsis* lines. The transgenic lines display a tolerant phenotype. Individual transformant lines are shown.
Figure 4:
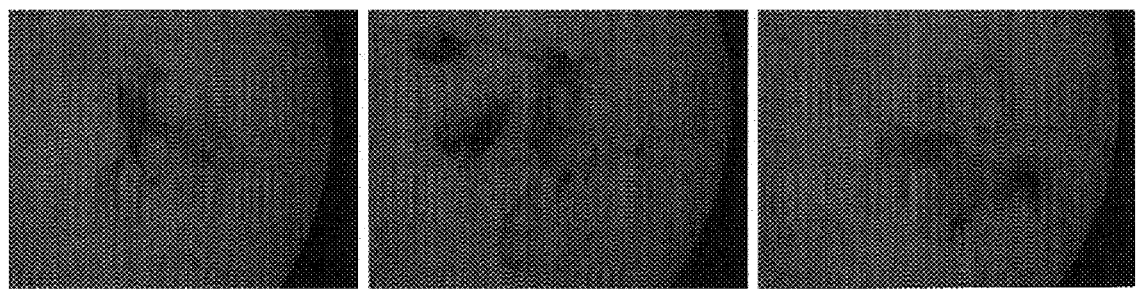
Figure 5:
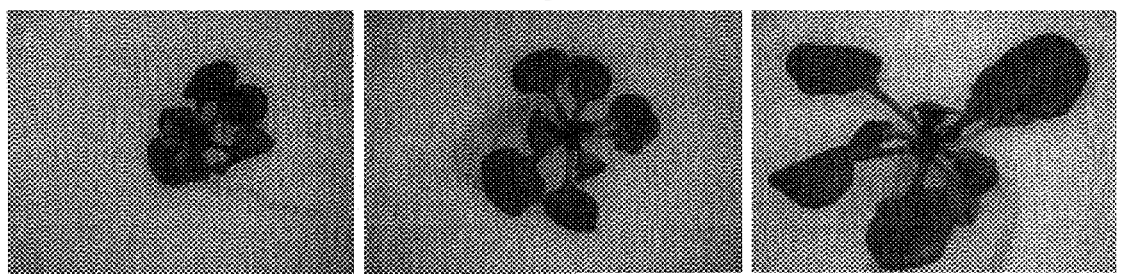
FIG. 5 show the results of a drought stress test with over-expressing PpGBP-4 transgenic plants and wild-type
Figure 5:
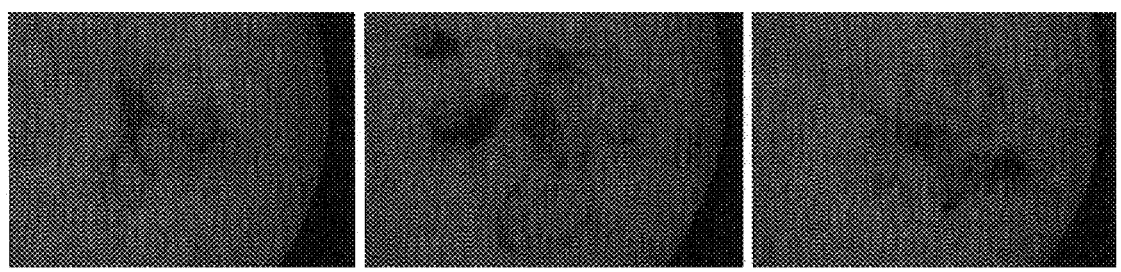
Figure 6:
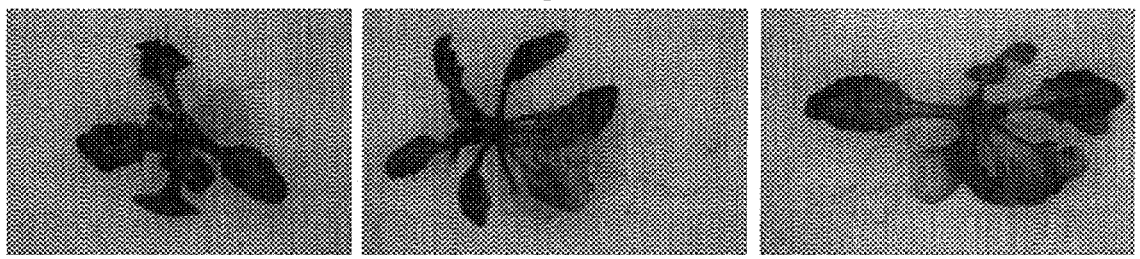
Figure 6:
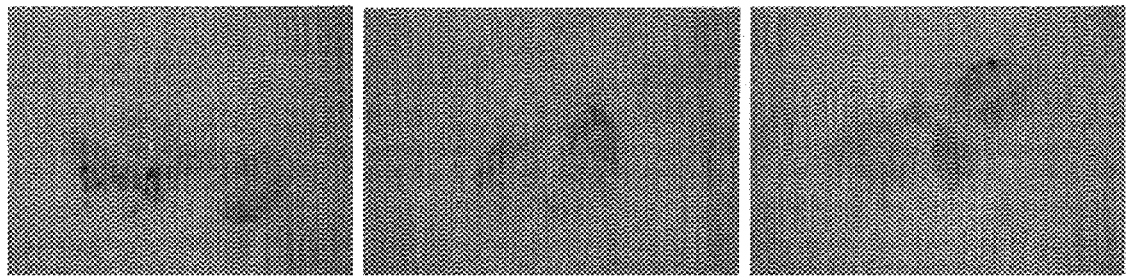

FIG. 6 show the results of a freezing stress test with over-expressing PpGBP-1 transgenic plants and wild-type *Arabidopsis* lines. The transgenic lines display a tolerant phenotype. Individual transformant lines are shown.

Figure 7:
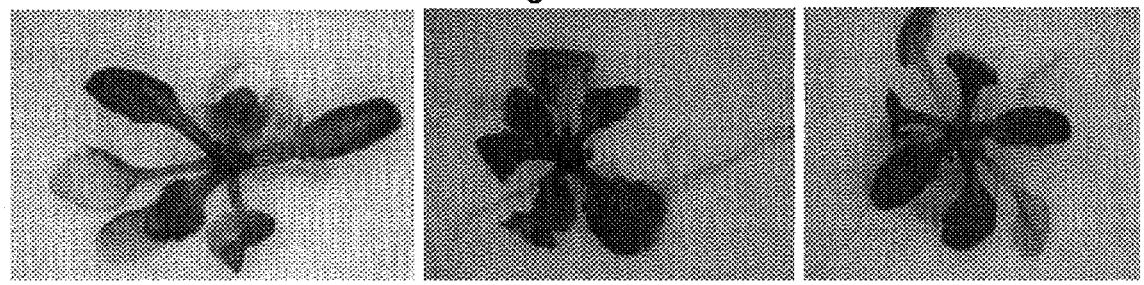
Figure 7:
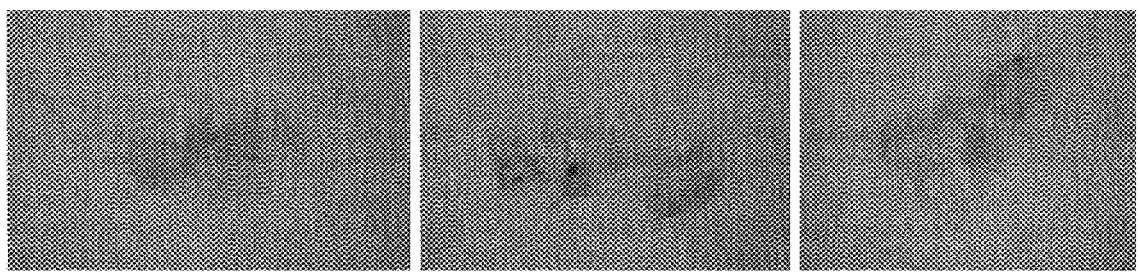

FIG. 7 show the results of a freezing stress test with over-expressing PpGBP-2 transgenic plants and wild-type *Arabidopsis* lines. The transgenic lines display a tolerant phenotype. Individual transformant lines are shown.

Figure 8:
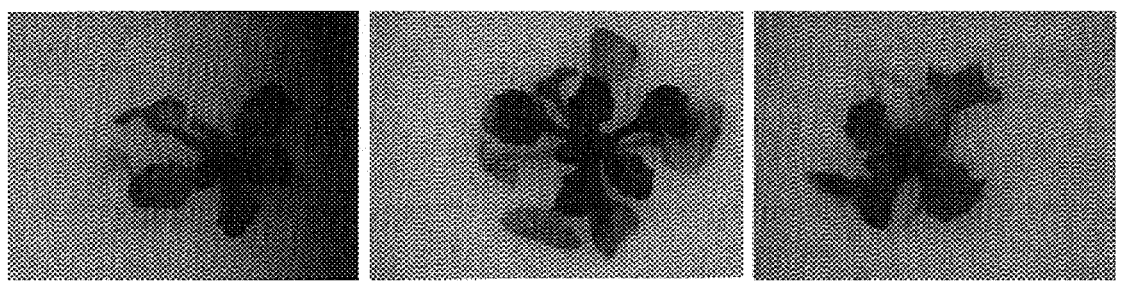
Figure 8:
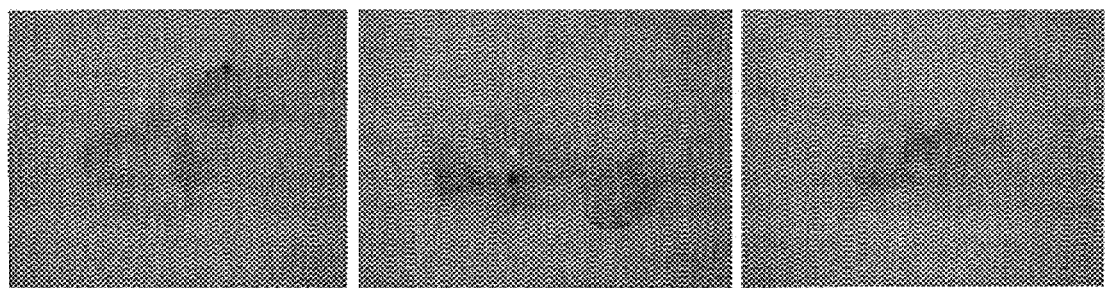

FIG. 8 show the results of a freezing stress test with over-expressing PpGBP-3 transgenic plants and wild-type *Arabidopsis* lines. The transgenic lines display a tolerant phenotype. Individual transformant lines are shown.

Figure 9:
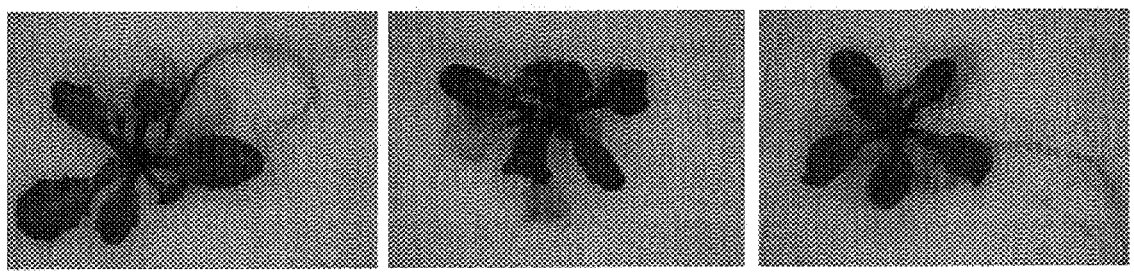
Figure 9:
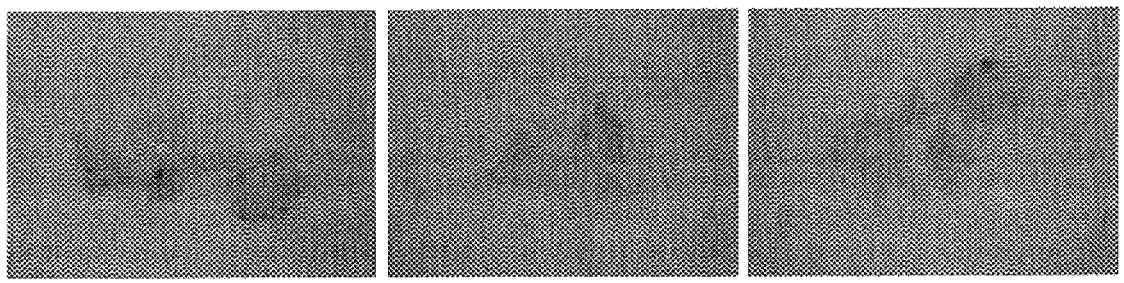

FIG. 9 show the results of a freezing stress test with over-expressing PpGBP-4 transgenic plants and wild-type *Arabidopsis* lines. The transgenic lines display a tolerant phenotype. Individual transformant lines are shown.

Figure 10:
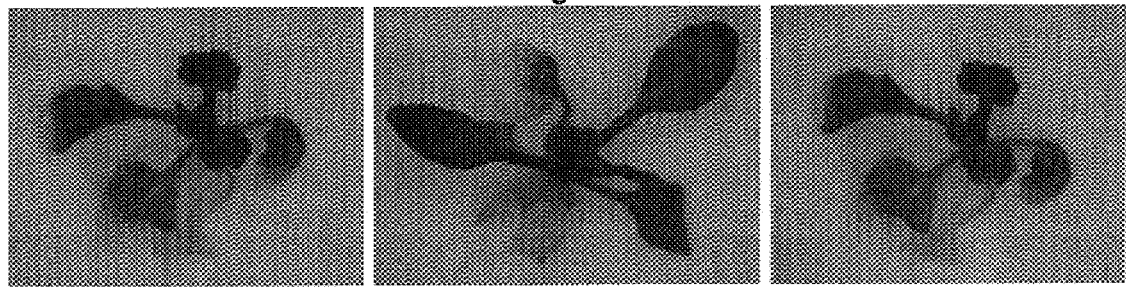
Figure 10:

FIG. 10 show the results of a freezing stress test with over-expressing PpGBP-5 transgenic plants and wild-type *Arabidopsis* lines. The transgenic lines display a tolerant phenotype. Individual transformant lines are shown.

DETAILED DESCRIPTION OF THE INVENTION

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as protein "GTP Binding Stress-Related Proteins" (GBSRPs), in no way limits the functionality of those sequences.

The present invention provides a transgenic plant cell transformed by a GBSRP coding nucleic acid, wherein expression of the nucleic acid sequence in the plant cell results in increased tolerance to environmental stress as compared to a wild type variety of the plant cell. The invention further provides transgenic plant parts and transgenic plants containing the plant cells described herein. Also provided is a plant seed produced by a transgenic plant transformed by a GBSRP coding nucleic acid, wherein the seed contains the GBSRP coding nucleic acid, and wherein the plant is true breeding for increased tolerance to environmental stress as compared to a wild type variety of the plant. The invention further provides a seed produced by a transgenic plant expressing a GBSRP, wherein the seed contains the GBSRP, and wherein the plant is true breeding for increased tolerance to environmental stress as compared to a wild type variety of the plant. The invention also provides an agricultural product produced by any of the below-described transgenic plants, plant parts and plant seeds.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* GBSRPs, GBP-1, GBP-2, GBP-3, GBP-4 and GBP-5, are useful for increasing a plant's tolerance to environmental stress. The predicted protein encoded by PpGBP-1 is similar to particular class of yeast small G-protein, the Sar-1 protein (Davies C. 1994. Plant Mol. Biol. 24:525–31). Sar1 is involved in yeast transport of vesicles in the endoplasmic reticulum. Additionally, the predicted protein encoded by PpGBP-3 is similar to members of the large family of Rab small G-proteins. These proteins have been implicated with recycling soluble ER proteins back to the lumen of the ER in mammalian systems (Chavrier P. et al. 1990 Cell 62:317–29). Moreover, Rab-like small G-proteins have been shown to be induced in plants upon onset of stress treatments (Bolte et al. 2000 Plant Mol. Biol. 42:923–36 and O'Mahony and Oliver 1999 Plant Mol. Biol. 39:809–21). Over-expression of this class of proteins can increase stress tolerance by preserving membrane integrity during the stress interval and accelerating membrane reconstruction upon cessation of stress.

Another novel predicted protein of the present invention is PpGBP-2. The GBP-2 protein is homologous to beta sub-units of heterodimeric G-proteins (Ishida S et al. 1993 PNAS 90:11152–6). Despite the notion that the activated alpha sub-unit of heterodimeric G-proteins is the only regulatory component of the G-protein complex, evidence in mounting that the beta sub-unit also interacts with the signal transduction machinery. In mammals, G-protein beta sub-units have been determined to interact with potassium channels and phospholipase A (Clapham D E and Neer E J 1993 Nature 365:403–6 and Iniguez-Lluhi J et al. 1993 Trends in Cell Biol. 3:230–6). In plants, there are data suggesting the involvement of G-proteins in the regulation of potassium channels in guard cells and mesophyll cells (Fairley-Gemot G and Assmann S M 1991 Pl. Cell 3:1037–44 and Li W and Assmann S M 1993 PNAS 90:262–6). Accordingly, it is hypothesized herein that the GBP-2 proteins are involved in the regulation of potassium channels in plant cells. Over-expression of this class of proteins can increase stress tolerance by regulating water loss during stress conditions.

Another novel predicted protein of the present invention is PpGBP-4. The GBP-4 protein has homology with a class of G-proteins where typical members are the Dynamins. As discussed above, Dynamins may play a role in increasing stress tolerance via facilitation of the formation of the cell plate during cytokinesis and involvement in chloroplast biogenesis. Yet another novel predicted protein described herein is a PpGBP-5 protein. The GBP-5 protein is homologous to members of the large family of Ran G-proteins (Coutavas E et al. 1993 Nature 366:585–7). Ran G-proteins have been found in mammalian as well as in plant systems and are associated with cell cycle processes.

Accordingly, the present invention provides isolated GBSRPs selected from the group consisting of GBP-1, GBP-2, GBP-3, GBP-4 and GBP-5, and homologs thereof. In preferred embodiments, the GBSRP is selected from 1) a GTP Binding Protein-1 (GBP-1) as defined in SEQ ID NO:11; 2) a GTP Binding Protein-1 (GBP-2) as defined in SEQ ID NO:12; 3) a GTP Binding Protein-3 (GBP-3) as defined in SEQ ID NO:13; 4) a GTP Binding Protein-4 (GBP-4) as defined in SEQ ID NO:14; and 5) a GTP Binding Protein-5 (GBP-5) as defined in SEQ ID NO:15 and homologs and orthologs thereof. Homologs and orthologs of the amino acid sequences are defined below.

The GBSRPs of the present invention are preferably produced by recombinant DNA techniques. For example, a nucleic acid molecule encoding the protein is cloned into an expression vector (as described above), the expression vector is introduced into a host cell (as described above) and the GBSRP is expressed in the host cell. The GBSRP can then be isolated from the cells by an appropriate purification scheme using standard protein purification techniques. Alternative to recombinant expression, a GBSRP polypeptide, or peptide can be synthesized chemically using standard peptide synthesis techniques. Moreover, native GBSRP can be isolated from cells (e.g., *Physcomitrella patens*), for example using an anti-GBSRP antibody, which can be produced by standard techniques utilizing a GBSRP or fragment thereof.

The invention further provides an isolated GBSRP coding nucleic acid. The present invention includes GBSRP coding nucleic acids that encode GBSRPs as described herein. In preferred embodiments, the GBSRP coding nucleic acid is selected from 1) a GTP Binding Protein-1 (GBP-1) nucleic acid as defined in SEQ ID NO:6; 2) a GTP Binding Protein-2 (GBP-2) nucleic acid as defined in SEQ ID NO:7; 3) a GTP Binding Protein-3 (GBP-3) nucleic acid as defined in SEQ ID NO:8; 4) a GTP Binding Protein-4 (GBP-4) nucleic acid as defined in SEQ ID NO:9; and 5) a GTP Binding Protein-5 (GBP-5) nucleic acid as defined in SEQ ID NO:10 and homologs and orthologs thereof. Homologs and orthologs of the nucleotide sequences are defined below. In one preferred embodiment, the nucleic acid and protein are isolated from the plant genus *Physcomitrella*. In another preferred embodiment, the nucleic acid and protein are from a *Physcomitrella patens* (*P. patens*) plant.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, or temperature, or combinations thereof, and in particular, can be high salinity, low water content or low temperature. It is also to be understood that as used in the specification and in the claims, "a" or "an" can mean one or more, depending upon the context in which it is used. Thus, for example, reference to "a cell" can mean that at least one cell can be utilized.

As also used herein, the terms "nucleic acid" and "nucleic acid molecule" are intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA.

An "isolated" nucleic acid molecule is one that is substantially separated from other nucleic acid molecules which are present in the natural source of the nucleic acid. Preferably, an "isolated" nucleic acid is free of some of the sequences which naturally flank the nucleic acid (i.e., sequences located at the 5' and 3' ends of the nucleic acid) in the genomic DNA of the organism from which the nucleic acid is derived. For example, in various embodiments, the isolated GBSRP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Physcomitrella patens* cell). Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A nucleic acid molecule of the present invention, e.g., a nucleic acid molecule having a nucleotide sequence of SEQ ID NO:6, SEQ ID NO:7, SEQ ID NO:8, SEQ ID NO:9, SEQ ID NO:10, or a portion thereof, can be isolated using standard molecular biology techniques and the sequence information provided herein. For example, a *P. patens* GBSRP cDNA can be isolated from a *P. patens* library using all or portion of one of the sequences of SEQ ID NO:1, SEQ ID NO:2, SEQ ID NO:3, SEQ ID NO:4 and SEQ ID NO:5. Moreover, a nucleic acid molecule encompassing all or a portion of one of the sequences of SEQ ID NO:1, SEQ ID NO:2, SEQ ID NO:3, SEQ ID NO:4 and SEQ ID NO:5 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:2, SEQ ID NO:3, SEQ ID NO:4 and SEQ ID NO:5. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a GBSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:6, SEQ ID NO:7, SEQ ID NO:8, SEQ ID NO:9 and SEQ ID NO:10. These cDNAs comprise sequences encoding the GBSRPs (i.e., the "coding region", indicated in Table 1), as well as 5' untranslated sequences and 3' untranslated sequences. It is to be understood that SEQ ID NO:6, SEQ ID NO:7, SEQ ID NO:8, SEQ ID NO:9 and SEQ ID NO:10 comprise both coding regions and 5' and 3' untranslated regions. Alternatively, the nucleic acid molecules of the present invention can comprise only the coding region of any of the sequences in SEQ ID NO:6, SEQ ID NO:7, SEQ ID NO:8, SEQ ID NO:9 or SEQ ID NO:10 or can contain whole genomic fragments isolated from genomic DNA. A coding region of these sequences is indicated as an "ORF position". The present invention also includes GBSRP coding nucleic acids that encode GBSRPs as described herein. Preferred is a GBSRP coding nucleic acid that encodes a GBSRP selected from the group consisting of, GBP-1 (SEQ ID NO:11), GBP-2 (SEQ ID NO:12), GBP-3 (SEQ ID NO:13), GBP-4 (SEQ ID NO:14) and GBP-5 (SEQ ID NO:15).

Moreover, the nucleic acid molecule of the invention can comprise only a portion of the coding region of one of the sequences in SEQ ID NO:6, SEQ ID NO:7, SEQ ID NO:8, SEQ ID NO:9 and SEQ ID NO:10, for example, a fragment which can be used as a probe or primer or a fragment encoding a biologically active portion of a GBSRP. The nucleotide sequences determined from the cloning of the GBSRP genes from *P. patens* allow for the generation of probes and primers designed for use in identifying and/or cloning GBSRP homologs in other cell types and organisms, as well as GBSRP homologs from other mosses and related species.

Portions of proteins encoded by the GBSRP nucleic acid molecules of the invention are preferably biologically active portions of one of the GBSRPs described herein. As used herein, the term "biologically active portion of" a GBSRP is intended to include a portion, e.g., a domain/motif, of a GBSRP that participates in a stress tolerance response in a plant, has an activity as set forth in Table 1, or participates in the transcription of a protein involved in a stress tolerance response in a plant. To determine whether a GBSRP, or a biologically active portion thereof, can participate in transcription of a protein involved in a stress tolerance response in a plant, or whether repression of a GBSRP results in increased stress tolerance in a plant, a stress analysis of a plant comprising the GBSRP may be performed. Such analysis methods are well known to those skilled in the art, as detailed in Example 7. More specifically, nucleic acid fragments encoding biologically active portions of a GBSRP can be prepared by isolating a portion of one of the sequences in SEQ ID NO:11, SEQ ID NO:12, SEQ ID NO:13, SEQ ID NO:14 and SEQ ID NO:15, expressing the encoded portion of the GBSRP or peptide (e.g., by recombinant expression in vitro) and assessing the activity of the encoded portion of the GBSRP or peptide.

Biologically active portions of a GBSRP are encompassed by the present invention and include peptides comprising amino acid sequences derived from the amino acid sequence of a GBSRP, e.g., an amino acid sequence of SEQ ID NO:11, SEQ ID NO:12, SEQ ID NO:13, SEQ ID NO:14 or SEQ ID NO:15, or the amino acid sequence of a protein homologous to a GBSRP, which include fewer amino acids than a full length GBSRP or the full length protein which is homologous to a GBSRP, and exhibit at least one activity of a GBSRP. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a GBSRP. Moreover, other biologically active portions in which other regions of the protein are deleted, can be prepared by recombinant techniques and evaluated for one or more of the activities described herein. Preferably, the biologically active portions of a GBSRP include one or more selected domains/motifs or portions thereof having biological activity.

The invention also provides GBSRP chimeric or fusion proteins. As used herein, a GBSRP "chimeric protein" or "fusion protein" comprises a GBSRP polypeptide operatively linked to a non-GBSRP polypeptide. A GBSRP polypeptide refers to a polypeptide having an amino acid sequence corresponding to a GBSRP, whereas a non-GBSRP polypeptide refers to a polypeptide having an amino acid sequence corresponding to a protein which is not substantially homologous to the GBSRP, e.g., a protein that is different from the GBSRP and is derived from the same or a different organism. Within the fusion protein, the term "operatively linked" is intended to indicate that the GBSRP polypeptide and the non-GBSRP polypeptide are fused to each other so that both sequences fulfill the proposed function attributed to the sequence used. The non-GBSRP polypeptide can be fused to the N-terminus or C-terminus of the GBSRP polypeptide. For example, in one embodiment, the fusion protein is a GST-GBSRP fusion protein in which the GBSRP sequences are fused to the C-terminus of the GST sequences. Such fusion proteins can facilitate the purification of recombinant GBSRPs. In another embodiment, the fusion protein is a GBSRP containing a heterologous signal sequence at its N-terminus. In certain host cells (e.g., mammalian host cells), expression and/or secretion of a GBSRP can be increased through use of a heterologous signal sequence.

Preferably, a GBSRP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, Eds. Ausubel et al. John Wiley & Sons: 1992). Moreover, many expression vectors are commercially available that already encode a fusion moiety (e.g., a GST polypeptide). A GBSRP encoding nucleic acid can be cloned into such an expression vector such that the fusion moiety is linked in-frame to the GBSRP.

In addition to fragments and fusion proteins of the GBSRPs described herein, the present invention includes homologs and analogs of naturally occurring GBSRPs and GBSRP encoding nucleic acids in a plant. "Homologs" are defined herein as two nucleic acids or proteins that have similar, or "homologous", nucleotide or amino acid sequences, respectively. Homologs include allelic variants, orthologs, paralogs, agonists and antagonists of GBSRPs as defined hereafter. The term "homolog" further encompasses nucleic acid molecules that differ from one of the nucleotide sequences shown in SEQ ID NO:6, SEQ ID NO:7, SEQ ID NO:8, SEQ ID NO:9 and SEQ ID NO:10 (and portions thereof) due to degeneracy of the genetic code and thus encode the same GBSRP as that encoded by the nucleotide sequences shown in SEQ ID NO:6, SEQ ID NO:7, SEQ ID NO:8, SEQ ID NO:9 or SEQ ID NO:10. As used herein a "naturally occurring" GBSRP refers to a GBSRP amino acid sequence that occurs in nature. Preferably, a naturally occurring GBSRP comprises an amino acid sequence selected from the group consisting of SEQ ID NO:11, SEQ ID NO:12, SEQ ID NO:13, SEQ ID NO:14 and SEQ ID NO:15.

An agonist of the GBSRP can retain substantially the same, or a subset, of the biological activities of the GBSRP. An antagonist of the GBSRP can inhibit one or more of the activities of the naturally occurring form of the GBSRP. For example, the GBSRP antagonist can competitively bind to a downstream or upstream member of the cell membrane component metabolic cascade that includes the GBSRP, or bind to a GBSRP that mediates transport of compounds across such membranes, thereby preventing translocation from taking place.

Nucleic acid molecules corresponding to natural allelic variants and analogs, orthologs and paralogs of a GBSRP cDNA can be isolated based on their identity to the *Physcomitrella patens* GBSRP nucleic acids described herein using GBSRP cDNAs, or a portion thereof, as a hybridization probe according to standard hybridization techniques under stringent hybridization conditions. In an alternative embodiment, homologs of the GBSRP can be identified by screening combinatorial libraries of mutants, e.g., truncation mutants, of the GBSRP for GBSRP agonist or antagonist activity. In one embodiment, a variegated library of GBSRP variants is generated by combinatorial mutagenesis at the nucleic acid level and is encoded by a variegated gene library. A variegated library of GBSRP variants can be produced by, for example, enzymatically ligating a mixture of synthetic oligonucleotides into gene sequences such that a degenerate set of potential GBSRP sequences is expressible as individual polypeptides, or alternatively, as a set of larger fusion proteins (e.g., for phage display) containing the set of GBSRP sequences therein. There are a variety of methods that can be used to produce libraries of potential GBSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential GBSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477).

In addition, libraries of fragments of the GBSRP coding regions can be used to generate a variegated population of GBSRP fragments for screening and subsequent selection of homologs of a GBSRP. In one embodiment, a library of coding sequence fragments can be generated by treating a double stranded PCR fragment of a GBSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the GBSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of GBSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify GBSRP homologs (Arkin and Yourvan, 1992 PNAS 89:7811–7815; Delgrave et al., 1993 Protein Engineering 6(3):327–331). In another embodiment, cell based assays can be exploited to analyze a variegated GBSRP library, using methods well known in the art. The present invention further provides a method of identifying a novel GBSRP, comprising (a) raising a specific antibody response to a GBSRP, or a fragment thereof, as described herein; (b) screening putative GBSRP material with the antibody, wherein specific binding of the antibody to the material indicates the presence of a potentially novel GBSRP; and (c) analyzing the bound material in comparison to known GBSRP, to determine its novelty.

To determine the percent homology of two amino acid sequences (e.g., one of the sequences of SEQ ID NO:11, SEQ ID NO:12, SEQ ID NO:13, SEQ ID NO:14 and SEQ ID NO:15 and a mutant form thereof), the sequences are aligned for optimal comparison purposes (e.g., gaps can be introduced in the sequence of one protein or nucleic acid for optimal alignment with the other protein or nucleic acid). The amino acid residues at corresponding amino acid positions are then compared. When a position in one sequence (e.g., one of the sequences of SEQ ID NO:11, SEQ ID NO:12, SEQ ID NO:13, SEQ ID NO:14 and SEQ ID NO:15) is occupied by the same amino acid residue as the corresponding position in the other sequence (e.g., a mutant form of the sequence selected from the polypeptide of SEQ ID NO:11, SEQ ID NO:12, SEQ ID NO:13, SEQ ID NO:14 and SEQ ID NO:15), then the molecules are homologous at that position (i.e., as used herein amino acid or nucleic acid "homology" is equivalent to amino acid or nucleic acid "identity"). The same type of comparison can be made between two nucleic acid sequences.

The percent homology between the two sequences is a function of the number of identical positions shared by the sequences (i.e., % homology=numbers of identical positions/total numbers of positions×100). Preferably, the amino acid sequences included in the present invention are at least about 50–60%, preferably at least about 60–70%, and more preferably at least about 70–80%, 80–90%, 90–95%, and most preferably at least about 96%, 97%, 98%, 99% or more homologous to an entire amino acid sequence shown in SEQ ID NO:11, SEQ ID NO:12, SEQ ID NO:13, SEQ ID NO:14 or SEQ ID NO:15. In yet another embodiment, at least about 50–60%, preferably at least about 60–70%, and more preferably at least about 70–80%, 80–90%, 90–95%, and most preferably at least about 96%, 97%, 98%, 99% or more homologous to an entire amino acid sequence encoded by a nucleic acid sequence shown in SEQ ID NO:6, SEQ ID NO:7, SEQ ID NO:8, SEQ ID NO:9 or SEQ ID NO:10. In other embodiments, the preferable length of sequence comparison for proteins is at least 15 amino acid residues, more preferably at least 25 amino acid residues, and most preferably at least 35 amino acid residues.

In another preferred embodiment, an isolated nucleic acid molecule of the invention comprises a nucleotide sequence which is at least about 50–60%, preferably at least about 60–70%, more preferably at least about 70–80%, 80–90%, or 90–95%, and even more preferably at least about 95%, 96%, 97%, 98%, 99% or more homologous to a nucleotide sequence shown in SEQ ID NO:6, SEQ ID NO:7, SEQ ID NO:8, SEQ ID NO:9 or SEQ ID NO:10, or a portion thereof.

The preferable length of sequence comparison for nucleic acids is at least 75 nucleotides, more preferably at least 100 nucleotides and most preferably the entire length of the coding region.

It is also preferable that the homologous nucleic acid molecule of the invention encodes a protein or portion thereof which includes an amino acid sequence which is sufficiently homologous to an amino acid sequence of SEQ ID NO:11, SEQ ID NO:12, SEQ ID NO:13, SEQ ID NO:14 or SEQ ID NO:15 such that the protein or portion thereof maintains the same or a similar function as the amino acid sequence to which it is compared. Functions of the GBSRP amino acid sequences of the present invention include the ability to participate in a stress tolerance response in a plant, or more particularly, to participate in the transcription of a protein involved in a stress tolerance response in a *Physcomitrella patens* plant. Examples of such activities are described in Table 1.

In addition to the above-described methods, a determination of the percent homology between two sequences can be accomplished using a mathematical algorithm. A preferred, non-limiting example of a mathematical algorithm utilized for the comparison of two sequences is the algorithm of Karlin and Altschul (1990 Proc. Natl. Acad. Sci. USA 90:5873–5877). Such an algorithm is incorporated into the NBLAST and XBLAST programs of Altschul, et al. (1990 J. Mol. Biol. 215:403–410).

BLAST nucleic acid searches can be performed with the NBLAST program, score=100, wordlength=12 to obtain nucleic acid sequences homologous to the GBSRP nucleic acid molecules of the invention. Additionally, BLAST protein searches can be performed with the XBLAST program, score=50, wordlength=3 to obtain amino acid sequences homologous to GBSRPs of the present invention. To obtain gapped alignments for comparison purposes, Gapped BLAST can be utilized as described in Altschul et al. (1997 Nucleic Acids Res. 25:3389–3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used to obtain amino acid sequences homologous to the GBSRPs of the present invention. To obtain gapped alignments for comparison purposes, Gapped BLAST can be utilized as described in Altschul et al. (1997 Nucleic Acids Res. 25:3389–3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

Finally, homology between nucleic acid sequences can also be determined using hybridization techniques known to those of skill in the art. Accordingly, an isolated nucleic acid molecule of the invention comprises a nucleotide sequence which hybridizes, e.g., hybridizes under stringent conditions, to one of the nucleotide sequences shown in SEQ ID NO:6, SEQ ID NO:7, SEQ ID NO:8, SEQ ID NO:9 and SEQ ID NO:10, or a portion thereof. More particularly, an isolated nucleic acid molecule of the invention is at least 15 nucleotides in length and hybridizes under stringent conditions to the nucleic acid molecule comprising a nucleotide sequence of SEQ ID NO:6, SEQ ID NO:7, SEQ ID NO:8, SEQ ID NO:9 or SEQ ID NO:10. In other embodiments, the nucleic acid is at least 30, 50, 100, 250 or more nucleotides in length.

As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, 6.3.1–6.3.6, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to a sequence of SEQ ID NO:6, SEQ ID NO:7, SEQ ID NO:8, SEQ ID NO:9 or SEQ ID NO:10 corresponds to a naturally occurring nucleic acid molecule. As used herein, a "naturally occurring" nucleic acid molecule refers to an RNA or DNA molecule having a nucleotide sequence that occurs in nature (e.g., encodes a natural protein). In one embodiment, the nucleic acid encodes a naturally occurring *Physcomitrella patens* GBSRP.

Using the above-described methods, and others known to those of skill in the art, one of ordinary skill in the art can isolate homologs of the GBSRPs comprising amino acid sequences shown in SEQ ID NO:11, SEQ ID NO:12, SEQ ID NO:13, SEQ ID NO:14 or SEQ ID NO:15. One subset of these homologs is allelic variants. As used herein, the term "allelic variant" refers to a nucleotide sequence containing polymorphisms that lead to changes in the amino acid sequences of a GBSRP and that exist within a natural population (e.g., a plant species or variety). Such natural allelic variations can typically result in 1–5% variance in a GBSRP nucleic acid. Allelic variants can be identified by sequencing the nucleic acid sequence of interest in a number of different plants, which can be readily carried out by using hybridization probes to identify the same GBSRP genetic locus in those plants. Any and all such nucleic acid variations and resulting amino acid polymorphisms or variations in a GBSRP that are the result of natural allelic variation and that do not alter the functional activity of a GBSRP, are intended to be within the scope of the invention.

Moreover, nucleic acid molecules encoding GBSRPs from the same or other species such as GBSRP analogs, orthologs and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode proteins having the same or similar functions. As also used herein, the term "paralogs" refers to two nucleic acids that are related by duplication within a genome. Paralogs usually have different functions, but these functions may be related (Tatusov, R. L. et al. 1997 Science 278(5338):631–637). Analogs, orthologs and paralogs of a naturally occurring GBSRP can differ from the naturally occurring GBSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80–85%, more preferably 90%, and most preferably 95%, 96%, 97%, 98% or even 99% identity or homology with all or part of a naturally occurring GBSRP amino acid sequence and will exhibit a function similar to a GBSRP. Orthologs of the present invention are also preferably capable of participating in the stress response in plants. In one embodiment, the GBSRP orthologs maintain the ability to participate in the metabolism of compounds necessary for the construction of cellular membranes in *Physcomitrella patens*, or in the transport of molecules across these membranes.

In addition to naturally-occurring variants of a GBSRP sequence that may exist in the population, the skilled artisan will further appreciate that changes can be introduced by mutation into a nucleotide sequence of SEQ ID NO:6, SEQ ID NO:7, SEQ ID NO:8, SEQ ID NO:9 or SEQ ID NO:10, thereby leading to changes in the amino acid sequence of the encoded GBSRP, without altering the functional ability of the GBSRP. For example, nucleotide substitutions leading to amino acid substitutions at "non-essential" amino acid residues can be made in a sequence of SEQ ID NO:6, SEQ ID NO:7, SEQ ID NO:8, SEQ ID NO:9 or SEQ ID NO:10. A "non-essential" amino acid residue is a residue that can be altered from the wild-type sequence of one of the GBSRPs without altering the activity of said GBSRP, whereas an "essential" amino acid residue is required for GBSRP activity. Other amino acid residues, however, (e.g., those that are not conserved or only semi-conserved in the domain having GBSRP activity) may not be essential for activity and thus are likely to be amenable to alteration without altering GBSRP activity.

Accordingly, another aspect of the invention pertains to nucleic acid molecules encoding GBSRPs that contain changes in amino acid residues that are not essential for GBSRP activity. Such GBSRPs differ in amino acid sequence from a sequence contained in SEQ ID NO:11, SEQ ID NO:12, SEQ ID NO:13, SEQ ID NO:14 or SEQ ID NO:15, yet retain at least one of the GBSRP activities described herein. In one embodiment, the isolated nucleic acid molecule comprises a nucleotide sequence encoding a protein, wherein the protein comprises an amino acid sequence at least about 50% homologous to an amino acid sequence of SEQ ID NO:11, SEQ ID NO:12, SEQ ID NO:13, SEQ ID NO:14 or SEQ ID NO:15. Preferably, the protein encoded by the nucleic acid molecule is at least about 50–60% homologous to one of the sequences of SEQ ID NO:11, SEQ ID NO:12, SEQ ID NO:13, SEQ ID NO:14 and SEQ ID NO:15, more preferably at least about 60–70% homologous to one of the sequences of SEQ ID NO:11, SEQ ID NO:12, SEQ ID NO:13, SEQ ID NO:14 and SEQ ID NO:15, even more preferably at least about 70–80%, 80–90%, 90–95% homologous to one of the sequences of SEQ ID NO:11, SEQ ID NO:12, SEQ ID NO:13, SEQ ID NO:14 and SEQ ID NO:15, and most preferably at least about 96%, 97%, 98%, or 99% homologous to one of the sequences of SEQ ID NO:11, SEQ ID NO:12, SEQ ID NO:13, SEQ ID NO:14 and SEQ ID NO:15. The preferred GBSRP homologs of the present invention are preferably capable of participating in the stress tolerance response in a plant, or more particularly, participating in the transcription of a protein involved in a stress tolerance response in a *Physcomitrella patens* plant, or have one or more activities set forth in Table 1.

An isolated nucleic acid molecule encoding a GBSRP homologous to a protein sequence of SEQ ID NO:11, SEQ ID NO:12, SEQ ID NO:13, SEQ ID NO:14 or SEQ ID NO:15 can be created by introducing one or more nucleotide substitutions, additions or deletions into a nucleotide sequence of SEQ ID NO:6, SEQ ID NO:7, SEQ ID NO:8, SEQ ID NO:9 or SEQ ID NO:10 such that one or more amino acid substitutions, additions or deletions are introduced into the encoded protein. Mutations can be introduced into one of the sequences of SEQ ID NO:6, SEQ ID NO:7, SEQ ID NO:8, SEQ ID NO:9 and SEQ ID NO:10 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a GBSRP is preferably replaced with another amino acid residue from the same side chain family. Alternatively, in another embodiment, mutations can be introduced randomly along all or part of a GBSRP coding sequence, such as by saturation mutagenesis, and the resultant mutants can be screened for a GBSRP activity described herein to identify mutants that retain GBSRP activity. Following mutagenesis of one of the sequences of SEQ ID NO:6, SEQ ID NO:7, SEQ ID NO:8, SEQ ID NO:9 and SEQ ID NO:10, the encoded protein can be expressed recombinantly and the activity of the protein can be determined by analyzing the stress tolerance of a plant expressing the protein as described in Example 7.

In addition to the nucleic acid molecules encoding the GBSRPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire GBSRP coding strand, or to only a portion thereof. In one embodiment, an antisense nucleic acid molecule is antisense to a "coding region" of the coding strand of a nucleotide sequence encoding a GBSRP. The term "coding region" refers to the region of the nucleotide sequence comprising codons that are translated into amino acid residues (e.g., the entire coding region of , , , comprises nucleotides 1 to . . . ). In another embodiment, the antisense nucleic acid molecule is antisense to a "noncoding region" of the coding strand of a nucleotide sequence encoding a GBSRP. The term "noncoding region" refers to 5' and 3' sequences that flank the coding region that are not translated into amino acids (i.e., also referred to as 5' and 3' untranslated regions).

In a preferred embodiment, an isolated nucleic acid molecule of the invention comprises a nucleic acid molecule which is a complement of one of the nucleotide sequences shown in SEQ ID NO:6, SEQ ID NO:7, SEQ ID NO:8, SEQ ID NO:9 and SEQ ID NO:10, or a portion thereof. A nucleic acid molecule that is complementary to one of the nucleotide sequences shown in SEQ ID NO:6, SEQ ID NO:7, SEQ ID NO:8, SEQ ID NO:9 and SEQ ID NO:10 is one which is sufficiently complementary to one of the nucleotide sequences shown in SEQ ID NO:6, SEQ ID NO:7, SEQ ID NO:8, SEQ ID NO:9 and SEQ ID NO:10 such that it can hybridize to one of the nucleotide sequences shown in SEQ ID NO:6, SEQ ID NO:7, SEQ ID NO:8, SEQ ID NO:9 and SEQ ID NO:10, thereby forming a stable duplex.

Given the coding strand sequences encoding the GBSRPs disclosed herein (e.g., the sequences set forth in SEQ ID NO:6, SEQ ID NO:7, SEQ ID NO:8, SEQ ID NO:9 and SEQ ID NO:10), antisense nucleic acids of the invention can be designed according to the rules of Watson and Crick base pairing. The antisense nucleic acid molecule can be complementary to the entire coding region of GBSRP mRNA, but more preferably is an oligonucleotide which is antisense to only a portion of the coding or noncoding region of GBSRP mRNA. For example, the antisense oligonucleotide can be complementary to the region surrounding the translation start site of GBSRP mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a GBSRP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625–6641). The antisense nucleic acid molecule can also comprise a 2'-o-methylribonucleotide (Inoue et al., 1987 Nucleic Acids Res. 15:6131–6148) or a chimeric RNA-DNA analogue (Inoue et al., 1987 FEBS Lett. 215: 327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes described in Haselhoff and Gerlach, 1988 Nature 334:585–591) can be used to catalytically cleave GBSRP mRNA transcripts to thereby inhibit translation of GBSRP mRNA. A ribozyme having specificity for a GBSRP-encoding nucleic acid can be designed based upon the nucleotide sequence of a GBSRP cDNA, as disclosed herein (i.e., SEQ ID NO:6, SEQ ID NO:7, SEQ ID NO:8, SEQ ID NO:9 or SEQ ID NO:10) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a GBSRP-encoding mRNA. See, e.g., Cech et al. U.S. Pat. No. 4,987,071 and Cech et al. U.S. Pat. No. 5,116,742. Alternatively, GBSRP mRNA can be used to select a catalytic RNA having a specific ribonuclease activity from a pool of RNA molecules. See, e.g., Bartel, D. and Szostak, J. W., 1993 Science 261:1411–1418.

Alternatively, GBSRP gene expression can be inhibited by targeting nucleotide sequences complementary to the regulatory region of a GBSRP nucleotide sequence (e.g., a GBSRP promoter and/or enhancer) to form triple helical structures that prevent transcription of a GBSRP gene in target cells. See generally, Helene, C., 1991 Anticancer Drug Des. 6(6):569–84; Helene, C. et al., 1992 Ann. N.Y. Acad. Sci. 660:27–36; and Maher, L. J., 1992 Bioassays 14(12): 807–15.

In addition to the GBSRP nucleic acids and proteins described above, the present invention encompasses these nucleic acids and proteins attached to a moiety. These moieties include, but are not limited to, detection moieties, hybridization moieties, purification moieties, delivery moieties, reaction moieties, binding moieties, and the like. One typical group of nucleic acids attached to a moiety includes probes and primers. The probes and primers typically comprise a region of nucleotide sequence that hybridizes under stringent conditions to at least about 12, preferably about 25, more preferably about 40, 50 or 75 consecutive nucleotides of a sense strand of one of the sequences set forth in SEQ ID NO:6, SEQ ID NO:7, SEQ ID NO:8, SEQ ID NO:9 and SEQ ID NO:10, an anti-sense sequence of one of the sequences set forth in SEQ ID NO:6, SEQ ID NO:7, SEQ ID NO:8, SEQ ID NO:9 and SEQ ID NO:10, or naturally occurring mutants thereof. Primers based on a nucleotide sequence of SEQ ID NO:6, SEQ ID NO:7, SEQ ID NO:8, SEQ ID NO:9 or SEQ ID NO:10 can be used in PCR reactions to clone GBSRP homologs. Probes based on the GBSRP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a GBSRP, such as by measuring a level of a GBSRP-encoding nucleic acid, in a sample of cells, e.g., detecting GBSRP mRNA levels or determining whether a genomic GBSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: New York). This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317–326. To assess the presence or relative quantity of protein translated from this mRNA, standard techniques, such as a Western blot, may be employed. These techniques are well known to one of ordinary skill in the art. (See, for example, Ausubel et al., 1988 Current Protocols in Molecular Biology, Wiley: New York).

The invention further provides an isolated recombinant expression vector comprising a GBSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89–108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., GBSRPs, mutant forms of GBSRPs, fusion proteins, etc.).

The recombinant expression vectors of the invention can be designed for expression of GBSRPs in prokaryotic or eukaryotic cells. For example, GBSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423–488; van den Hondel, C. A. M. J. J. et al., 1991 Heterologous gene expression in filamentous fungi, in: More Gene Manipulations in Fungi, J. W. Bennet & L. L. Lasure, eds., p. 396–428: Academic Press: San Diego; and van den Hondel, C. A. M. J. J. & Punt, P. J., 1991 Gene transfer systems and vector development for filamentous fungi, in: Applied Molecular Genetics of Fungi, Peberdy, J. F. et al., eds., p. 1–28, Cambridge University Press: Cambridge), algae (Falciatore et al., 1999 Marine Biotechnology 1(3):239–251), ciliates of the types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella, and Stylonychia, especially of the genus Stylonychia lemnae with vectors following a transformation method as described in WO 98/01572 and multicellular plant cells (see Schmidt, R. and Willmitzer, L., 1988 High efficiency *Agrobacterium tumefaciens*-mediated transformation of *Arabidopsis thaliana* leaf and cotyledon explants, Plant Cell Rep. 583–586); Plant Molecular Biology and Biotechnology, C Press, Boca Raton, Fla., chapter 6/7, S.71–119 (1993); F. F. White, B. Jenes et al., Techniques for Gene Transfer, in: Transgenic Plants, Vol. 1, Engineering and Utilization, eds. Kung und R. Wu, 128–43, Academic Press: 1993; Potrykus, 1991 Annu. Rev. Plant Physiol. Plant Molec. Biol. 42:205–225 and references cited therein) or mammalian cells. Suitable host cells are discussed further in Goeddel, *Gene Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of a recombinant protein; 2) to increase the solubility of a recombinant protein; and 3) to aid in the purification of a recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the GBSRP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant GBSRP unfused to GST can be recovered by cleavage of the fusion protein with thrombin.

Examples of suitable inducible non-fusion *E. coli* expression vectors include pTrc (Amann et al., 1988 Gene 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS 174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111–2118). Such alteration of nucleic acid sequences of the invention can be carried out by standard DNA synthesis techniques.

In another embodiment, the GBSRP expression vector is a yeast expression vector. Examples of vectors for expression in yeast *S. cerevisiae* include pYepSecl (Baldari, et al., 1987 Embo J. 6:229–234), pMFa (Kurjan and Herskowitz, 1982 Cell 30:933–943), pJRY88 (Schultz et al., 1987 Gene 54:113–123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1–28, Cambridge University Press: Cambridge.

Alternatively, the GBSRPs of the invention can be expressed in insect cells using baculovirus expression vectors. Baculovirus vectors available for expression of proteins in cultured insect cells (e.g., Sf 9 cells) include the pAc series (Smith et al., 1983 Mol. Cell Biol. 3:2156–2165) and the pVL series (Lucklow and Summers, 1989 Virology 170:31–39).

In yet another embodiment, a GBSRP nucleic acid of the invention is expressed in mammalian cells using a mammalian expression vector. Examples of mammalian expression vectors include pCDM8 (Seed, B., 1987 Nature 329:840) and pMT2PC (Kaufinan et al., 1987 EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* $2^{nd}$, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268–277), lymphoid-specific promoters (Calame and Eaton, 1988 Adv. Immunol. 43:235–275), in particular promoters of T cell receptors (Winoto and Baltimore, 1989 EMBO J. 8:729–733) and immunoglobulins (Banerji et al., 1983 Cell 33:729–740; Queen and Baltimore, 1983 Cell 33:741–748), neuron-specific promoters (e.g., the neurofilament promoter; Byrne and Ruddle, 1989 *PNAS* 86:5473–5477), pancreas-specific promoters (Edlund et al., 1985 Science 230:912–916), and mammary gland-specific promoters (e.g., milk whey promoter; U.S. Pat. No. 4,873,316 and European Application Publication No. 264,166). Developmentally regulated promoters are also encompassed, for example, the murine hox promoters (Kessel and Gruss, 1990 Science 249:374–379) and the fetoprotein promoter (Campes and Tilghman, 1989 Genes Dev. 3:537–546).

In another embodiment, the GBSRPs of the invention may be expressed in unicellular plant cells (such as algae) (see Falciatore et al., 1999 Marine Biotechnology 1(3): 239–251 and references therein) and plant cells from higher plants (e.g., the spermatophytes, such as crop plants). Examples of plant expression vectors include those detailed in: Becker, D., Kemper, E., Schell, J. and Masterson, R., 1992 New plant binary vectors with selectable markers located proximal to the left border, Plant Mol. Biol. 20: 1195–1197; and Bevan, M. W., 1984 Binary *Agrabacterium* vectors for plant transformation, Nucl. Acid. Res. 12:8711–8721; Vectors for Gene Transfer in Higher Plants; in: Transgenic Plants, Vol. 1, Engineering and Utilization, eds.: Kung and R. Wu, Academic Press, 1993, S. 15–38.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., 1987 Nucl. Acids Research 15:8693–8711).

Plant gene expression has to be operably linked to an appropriate promoter conferring gene expression in a timely, cell or tissue specific manner. Preferred are promoters driving constitutive expression (Benfey et al., 1989 EMBO J. 8:2195–2202) like those derived from plant viruses like the 35S CAMV (Franck et al., 1980 Cell 21:285–294), the 19S CaMV (see also U.S. Pat. No. 5352605 and PCT Application No. WO 8402913) or plant promoters like those from Rubisco small subunit described in U.S. Pat. No. 4,962,028.

Other preferred sequences for use in plant gene expression cassettes are targeting-sequences necessary to direct the gene product in its appropriate cell compartment (for review see Kermode, 1996 Crit. Rev. Plant Sci. 15(4):285–423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (see Gatz, 1997 Annu. Rev. Plant Physiol. Plant Mol. Biol. 48:89–108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992 Plant J. 2:397–404) and an ethanol inducible promoter (PCT Application No. WO 93/21334).

Also, suitable promoters responding to biotic or abiotic stress conditions are those such as the pathogen inducible PRPl-gene promoter (Ward et al., 1993 Plant. Mol. Biol. 22:361–366), the heat inducible hsp80-promoter from tomato (U.S. Pat. No. 5,187,267), cold inducible alpha-amylase promoter from potato (PCT Application No. WO 96/12814) or the wound-inducible pinII-promoter (European Patent No. 375091). For other examples of drought, cold, and salt-inducible promoters, such as the RD29A promoter, see Yamaguchi-Shinozalei et al. (1993 Mol. Gen. Genet. 236:331–340).

Especially preferred are those promoters that confer gene expression in specific tissues and organs, such as guard cells and the root hair cells. Suitable promoters include the napin-gene promoter from rapeseed (U.S. Pat. No. 5,608,152), the USP-promoter from *Vicia faba* (Baeumlein et al., 1991 Mol Gen Genet. 225(3):459–67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980) or the legumin B4 promoter (LeB4; Baeumlein et al., 1992 Plant Journal, 2(2):233–9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, maize zein gene, oat glutelin gene, *Sorghum* kasirin-gene and rye secalin gene).

Also especially suited are promoters that confer plastid-specific gene expression since plastids are the compartment where lipid biosynthesis occurs. Suitable promoters are the viral RNA-polymerase promoter described in PCT Application No. WO 95/16783 and PCT Application No. WO 97/06250 and the clpP-promoter from *Arabidopsis* described in PCT Application No. WO 99/46394.

The invention further provides a recombinant expression vector comprising a GBSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a GBSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus wherein antisense nucleic acids are produced under the control of a high efficiency regulatory region. The activity of the regulatory region can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986 and Mol et al., 1990 FEBS Letters 268:427–430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a GBSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

Vector DNA can be introduced into prokaryotic or eukaryotic cells via conventional transformation or transfection techniques. As used herein, the terms "transformation", "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer and electroporation. Suitable methods for transforming or transfecting host cells including plant cells can be found in Sambrook, et al. (Molecular Cloning: A Laboratory Manual. $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrabacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses and forage crops, these crop plants are also preferred target plants for a genetic engineering as one further embodiment of the present invention.

In particular, the invention provides a method of producing a transgenic plant with a GBSRP coding nucleic acid, wherein expression of the nucleic acid(s) in the plant results in increased tolerance to environmental stress as compared to a wild type variety of the plant comprising: (a) transforming a plant cell with an expression vector comprising a GBSRP nucleic acid, and (b) generating from the plant cell a transgenic plant with a increased tolerance to environmental stress as compared to a wild type variety of the plant. The invention also provides a method of increasing expression of a gene of interest within a host cell as compared to a wild type variety of the host cell, wherein the gene of interest is transcribed in response to a GBSRP, comprising: (a) transforming the host cell with an expression vector comprising a GBSRP coding nucleic acid, and (b) expressing the GBSRP within the host cell, thereby increasing the expression of the gene transcribed in response to the GBSRP, as compared to a wild type variety of the host cell.

For such plant transformation, binary vectors such as pBinAR can be used (Höfgen and Willmitzer, 1990 Plant Science 66:221–230). Construction of the binary vectors can be performed by ligation of the cDNA in sense or antisense orientation into the T-DNA. 5-prime to the cDNA a plant promoter activates transcription of the cDNA. A polyadenylation sequence is located 3-prime to the cDNA. Tissue-specific expression can be achieved by using a tissue specific promoter. For example, seed-specific expression can be achieved by cloning the napin or LeB4 or USP promoter 5-prime to the cDNA. Also, any other seed specific promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, 1996 Crit. Rev. Plant Sci. 4 (15):285–423). The signal peptide is cloned 5-prime in frame to the cDNA to archive subcellular localization of the fusion protein. Additionally, promoters that are responsive to abiotic stresses can be used with, such as the *Arabidopsis* promoter RD29A, the nucleic acid sequences disclosed herein. One skilled in the art will recognize that the promoter used should be operatively linked to the nucleic acid such that the promoter causes transcription of the nucleic acid that results in the synthesis of a mRNA that encodes a polypeptide. Alternatively, the RNA can be an antisense RNA for use in affecting subsequent expression of the same or another gene or genes.

Alternate methods of transfection include the direct transfer of DNA into developing flowers via electroporation or *Agrabacterium* mediated gene transfer. *Agrabacterium* mediated plant transformation can be performed using for example the GV3101(pMP90) (Koncz and Schell, 1986 Mol. Gen. Genet. 204:383–396) or LBA4404 (Clontech) *Agrobacterium tumefaciens* strain. Transformation can be performed by standard transformation and regeneration techniques (Deblaere et al., 1994 Nucl. Acids. Res. 13:4777–4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signature: BT11-P ISBN 0-7923-2731-4; Glick, Bernard R.; Thompson, John E., Methods in Plant Molecular Biology and Biotechnology, Boca Raton: CRC Press, 1993.—360 S.,ISBN 0-8493-5164-2). For example, rapeseed can be transformed via cotyledon or hypocotyl transformation (Moloney et al., 1989 Plant cell Report 8:238–242; De Block et al., 1989 Plant Physiol. 91:694–701). Use of antibiotica for *Agrabacterium* and plant selection depends on the binary vector and the *Agrabacterium* strain used for transformation. Rapeseed selection is normally performed using kanamycin as selectable plant marker. *Agrabacterium* mediated gene transfer to flax can be performed using, for example, a technique described by Mlynarova et al., 1994 Plant Cell Report 13:282–285. Additionally, transformation of soybean can be performed using for example a technique described in European Patent No. 0424 047, U.S. Pat. No. 5,322,783, European Patent No. 0397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding a GBSRP or can be introduced on a separate vector. Cells stably transfected with the introduced nucleic acid molecule can be identified by, for example, drug selection (e.g., cells that have incorporated the selectable marker gene will survive, while the other cells die).

To create a homologous recombinant microorganism, a vector is prepared which contains at least a portion of a GBSRP gene into which a deletion, addition or substitution has been introduced to thereby alter, e.g., functionally disrupt, the GBSRP gene. Preferably, the GBSRP gene is a *Physcomitrella patens* GBSRP gene, but it can be a homolog from a related plant or even from a mammalian, yeast, or insect source. In a preferred embodiment, the vector is designed such that, upon homologous recombination, the endogenous GBSRP gene is functionally disrupted (i.e., no longer encodes a functional protein; also referred to as a knock-out vector). Alternatively, the vector can be designed such that, upon homologous recombination, the endogenous GBSRP gene is mutated or otherwise altered but still encodes a functional protein (e.g., the upstream regulatory region can be altered to thereby alter the expression of the endogenous GBSRP). To create a point mutation via homologous recombination, DNA-RNA hybrids can be used in a technique known as chimeraplasty (Cole-Strauss et al., 1999 Nucleic Acids Research 27(5):1323–1330 and Kmiec, 1999 Gene therapy American Scientist 87(3):240–247). Homologous recombination procedures in *Physcomitrella patens* are also well known in the art and are contemplated for use herein.

Whereas in the homologous recombination vector, the altered portion of the GBSRP gene is flanked at its 5' and 3' ends by an additional nucleic acid molecule of the GBSRP gene to allow for homologous recombination to occur between the exogenous GBSRP gene carried by the vector and an endogenous GBSRP gene, in a microorganism or plant. The additional flanking GBSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8):4368–4373 for cDNA based recombination in *Physcomitrella patens*). The vector is introduced into a microorganism or plant cell (e.g., via polyethylene glycol mediated DNA), and cells in which the introduced GBSRP gene has homologously recombined with the endogenous GBSRP gene are selected using art-known techniques.

In another embodiment, recombinant microorganisms can be produced that contain selected systems that allow for regulated expression of the introduced gene. For example, inclusion of a GBSRP gene on a vector placing it under control of the lac operon permits expression of the GBSRP gene only in the presence of IPTG. Such regulatory systems are well known in the art.

A host cell of the invention, such as a prokaryotic or eukaryotic host cell in culture, can be used to produce (i.e., express) a GBSRP. Accordingly, the invention further provides methods for producing GBSRPs using the host cells of the invention. In one embodiment, the method comprises culturing the host cell of invention (into which a recombinant expression vector encoding a GBSRP has been introduced, or into which genome has been introduced a gene encoding a wild-type or altered GBSRP) in a suitable medium until GBSRP is produced. In another embodiment, the method further comprises isolating GBSRPs from the medium or the host cell.

Another aspect of the invention pertains to isolated GBSRPs, and biologically active portions thereof. An "isolated" or "purified" protein or biologically active portion thereof is free of some of the cellular material when produced by recombinant DNA techniques, or chemical precursors or other chemicals when chemically synthesized. The language "substantially free of cellular material" includes preparations of GBSRP in which the protein is separated from some of the cellular components of the cells in which it is naturally or recombinantly produced. In one embodiment, the language "substantially free of cellular material" includes preparations of a GBSRP having less than about 30% (by dry weight) of non-GBSRP material (also referred to herein as a "contaminating protein"), more preferably less than about 20% of non-GBSRP material, still more preferably less than about 10% of non-GBSRP material, and most preferably less than about 5% non-GBSRP material.

When the GBSRP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of GBSRP in which the protein is separated from chemical precursors or other chemicals that are involved in the synthesis of the protein. In one embodiment, the language "substantially free of chemical precursors or other chemicals" includes preparations of a GBSRP having less than about 30% (by dry weight) of chemical precursors or non-GBSRP chemicals, more preferably less than about 20% chemical precursors or non-GBSRP chemicals, still more preferably less than about 10% chemical precursors or non-GBSRP chemicals, and most preferably less than about 5% chemical precursors or non-GBSRP chemicals. In preferred embodiments, isolated proteins, or biologically active portions thereof, lack contaminating proteins from the same organism from which the GBSRP is derived. Typically, such proteins are produced by recombinant expression of, for example, a *Physcomitrella patens* GBSRP in plants other than *Physcomitrella patens* or microorganisms such as *C. glutamicum*, ciliates, algae or fungi.

The nucleic acid molecules, proteins, protein homologs, fusion proteins, primers, vectors, and host cells described herein can be used in one or more of the following methods: identification of *Physcomitrella patens* and related organisms; mapping of genomes of organisms related to *Physcomitrella patens*; identification and localization of *Physcomitrella patens* sequences of interest; evolutionary studies; determination of GBSRP regions required for function; modulation of a GBSRP activity; modulation of the metabolism of one or more cell functions; modulation of the transmembrane transport of one or more compounds; and modulation of stress resistance.

The moss *Physcomitrella patens* represents one member of the mosses. It is related to other mosses such as *Ceratodon purpureus* that is capable of growth in the absence of light. Mosses like Ceratodon and *Physcomitrella* share a high degree of homology on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The GBSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a GBSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and forage crops, for example.

In particular, the present invention describes using the expression of GBP-1, GBP-2, GBP-3, GBP-4 and GBP-5 of *Physcomitrella patens* to engineer drought-tolerant, salt-tolerant and/or cold-tolerant plants. This strategy has herein been demonstrated for *Arabidopsis thaliana*, Rapeseed/Canola, soybeans, corn and wheat but its application is not restricted to these plants. Accordingly, the invention provides a transgenic plant containing a GBSRP selected from GBP-1 (SEQ ID NO:11), GBP-2 (SEQ ID NO:12), GBP-3 (SEQ ID NO:13), GBP-4 (SEQ ID NO:14) and GBP-5 (SEQ ID NO:15), wherein the environmental stress is drought, increased salt or decreased or increased temperature. In preferred embodiments, the environmental stress is drought or decreased temperature.

The present invention also provides methods of modifying stress tolerance of a plant comprising, modifying the expression of a GBSRP in the plant. The invention provides that this method can be performed such that the stress tolerance is either increased or decreased. In particular, the present invention provides methods of producing a transgenic plant having an increased tolerance to environmental stress as compared to a wild type variety of the plant comprising increasing expression of a GBSRP in a plant.

The methods of increasing expression of GBSRPs can be used wherein the plant is either transgenic or not transgenic. In cases when the plant is transgenic, the plant can be transformed with a vector containing any of the above described GBSRP coding nucleic acids, or the plant can be transformed with a promoter that directs expression of native GBSRP in the plant, for example. The invention provides that such a promoter can be tissue specific. Furthermore, such a promoter can be developmentally regulated. Alternatively, non-transgenic plants can have native GBSRP expression modified by inducing a native promoter.

The expression of GBP-1 (SEQ ID NO:6), GBP-2 (SEQ ID NO:7), GBP-3 (SEQ ID NO:8), GBP-4 (SEQ ID NO:9) or GBP-5 (SEQ ID NO:10) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657). The later case involves identification of the GBP-1 (SEQ ID NO:11), GBP-2 (SEQ ID NO:12), GBP-3 (SEQ ID NO:13), GBP-4 (SEQ ID NO:14) or GBP-5 (SEQ ID NO:15) homologs in the target plant as well as from its promoter. Zinc-finger-containing recombinant transcription factors are engineered to specifically interact with the GBP-1 (SEQ ID NO:11), GBP-2 (SEQ ID NO:12), GBP-3 (SEQ ID NO:13), GBP-4 (SEQ ID NO:14) or GBP-5 (SEQ ID NO:15) homolog and transcription of the corresponding gene is activated.

In addition to introducing the GBSRP nucleic acid sequences into transgenic plants, these sequences can also be used to identify an organism as being *Physcomitrella patens* or a close relative thereof. Also, they may be used to identify the presence of *Physcomitrella patens* or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene that is unique to this organism, one can ascertain whether this organism is present.

Further, the nucleic acid and protein molecules of the invention may serve as markers for specific regions of the genome. This has utility not only in the mapping of the genome, but also in functional studies of *Physcomitrella patens* proteins. For example, to identify the region of the genome to which a particular *Physcomitrella patens* DNA-binding protein binds, the *Physcomitrella patens* genome could be digested, and the fragments incubated with the DNA-binding protein. Those fragments that bind the protein may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses.

The GBSRP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein that are essential for the functioning of the enzyme. This type of determination is of value for protein engineering studies and may give an indication of what the protein can tolerate in terms of mutagenesis without losing function.

Manipulation of the GBSRP nucleic acid molecules of the invention may result in the production of GBSRPs having functional differences from the wild-type GBSRPs. These proteins may be improved in efficiency or activity, may be present in greater numbers in the cell than is usual, or may be decreased in efficiency or activity.

There are a number of mechanisms by which the alteration of a GBSRP of the invention may directly affect stress response and/or stress tolerance. In the case of plants expressing GBSRPs, increased transport can lead to improved salt and/or solute partitioning within the plant tissue and organs. By either increasing the number or the activity of transporter molecules that export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469–714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1–27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their tolerance to drought, salt, and temperature stress.

The engineering of one or more GBSRP genes of the invention may also result in GBSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226–235). While these products are typically excreted, cells can be genetically altered to transport more products than is typical for a wild-type cell. By optimizing the activity of one or more GBSRPs of the invention that are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998 The Plant Journal 15:39–48). The resultant knockout cells can then be evaluated for their ability or capacity to tolerate various stress conditions, their response to various stress conditions, and the effect on the phenotype and/or genotype of the mutation. For other methods of gene inactivation see U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246–252.

The aforementioned mutagenesis strategies for GBSRPs resulting in increased stress resistance are not meant to be limiting; variations on these strategies will be readily apparent to one skilled in the art. Using such strategies, and incorporating the mechanisms disclosed herein, the nucleic acid and protein molecules of the invention may be utilized to generate algae, ciliates, plants, fungi or other microorganisms like *C. glutamicum* expressing mutated GBSRP nucleic acid and protein molecules such that the stress tolerance is improved.

The present invention also provides antibodies that specifically bind to a GBSRP, or a portion thereof, as encoded by a nucleic acid described herein. Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163–167; Bebbington et al., 1992 Bio/Technology 10:169–175).

The phrases "selectively binds" and "specifically binds" with the polypeptide refer to a binding reaction that is determinative of the presence of the protein in a heterogeneous population of proteins and other biologics. Thus, under designated immunoassay conditions, the specified antibodies bound to a particular protein do not bind in a significant amount to other proteins present in the sample. Selective binding of an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See *Harlow and Lane* "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B.S.G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438–446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol $s^{-1} m^{-2}$ (white light; Philips TL 65W/25 fluorescent tube) and a light/dark change of 16/8 hours. The moss was either modified in liquid culture using Knop medium according to Reski and Abel (1985, Planta 165:354–358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of $H_2O$+RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al. 1994, Mol. Gen. Genet., 244:352–359). The Poly(A)+ RNA was isolated using Dyna Beads$^R$ (Dynal, Oslo, Norway) following the instructions of the manufacturers protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands. Plasmid DNA was prepared from overnight grown *E. coli* cultures grown in Luria-Broth medium containing ampicillin (see Sambrook et al. 1989 Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

| | | |
|---|---|---|
| 5'-CAGGAAACAGCTATGACC-3' | | SEQ ID NO:16 |
| 5'-CTAAAGGGAACAAAAGCTG-3' | | SEQ ID NO:17 |
| 5'-TGTAAAACGACGGCCAGT-3' | | SEQ ID NO:18 |

Sequences were processed and annotated using the software package EST-MAX commercially provided by Bio-Max (Munich, Germany). The program incorporates practically all bioinformatics methods important for functional and structural characterization of protein sequences. For reference the website at pedant.mips.biochem.mpg.de. The most important algorithms incorporated in EST-MAX are: FASTA: Very sensitive sequence database searches with estimates of statistical significance; Pearson W. R. (1990) Rapid and sensitive sequence comparison with FASTP and FASTA. Methods Enzymol. 183:63–98; BLAST: Very sensitive sequence database searches with estimates of statistical significance. Altschul S. F., Gish W., Miller W., Myers E. W., and Lipman D. J. Basic local alignment search tool. Journal of Molecular Biology 215:403–10; PREDATOR: High-accuracy secondary structure prediction from single and multiple sequences. Frishman, D. and Argos, P. (1997) 75% accuracy in protein secondary structure prediction. Proteins, 27:329–335; CLUSTALW: Multiple sequence alignment. Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673–4680; TMAP: Transmembrane region prediction from multiply aligned sequences. Persson, B. and Argos, P. (1994) Prediction of transmembrane segments in proteins utilizing multiple sequence alignments. J. Mol. Biol. 237:182–192; ALOM2: Transmembrane region prediction from single sequences. Klein, P., Kanehisa, M., and DeLisi, C. Prediction of protein function from sequence properties: A discriminate analysis of a database. Biochim. Biophys. Acta 787:221–226 (1984). Version 2 by Dr. K. Nakai; PROSEARCH: Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919–921; BLIMPS: Similarity searches against a database of ungapped blocks. J. C. Wallace and Henikoff S., (1992); PATMAT: A searching and extraction program for sequence, pattern and block queries and databases, CABIOS 8:249–254. Written by Bill Alford.

Example 5

Identification of *Physcomitrella patens* ORFs Corresponding to GBP-1, GBP-2, GBP-3, GBP-4 and GBP-5

The *Physcomitrella patens* partial cDNAs (ESTs) shown in Table 1 below were identified in the *Physcomitrella patens* EST sequencing program using the program EST-MAX through BLAST analysis. The Sequence Identification Numbers corresponding to these ESTs are as follows: GBP-1 (SEQ ID NO:1), GBP-2 (SEQ ID NO:2), GBP-3 (SEQ ID NO:3), GBP-4 (SEQ ID NO:4) and GBP-5 (SEQ ID NO:5). Tables 2–6 show proteins homologous to each of the GBSRPs.

TABLE 1

| Name | Functional categories | Function | Sequence code | ORF position |
|---|---|---|---|---|
| PpGBP-1 | GTP-binding proteins | GTP-binding protein | c_pp001077008r | 803–177 |
| Pp-GBP-2 | GTP-binding proteins | GTP-binding regulatory protein beta chain homolog | c_pp004025198r | 44–670 |
| Pp-GBP-3 | GTP-binding proteins | ras-related protein p2 | c_pp004055272r | 574–266 |
| Pp-GBP-4 | GTP-binding proteins | phragmoplastin 5 | c_pp004071064r | 1–251 |
| PpGBP-5 | GTP-binding proteins | GTP-binding protein RanBP1b homolog T27E13.20 | s_pp004063374r | 43–489 |

TABLE 2

Degree of amino acid identity and similarity of PpGBP-1 and other homologous proteins (Pairwise comparison program was used: gap penalty: 10; gap extension penalty: 0.1; score matrix: blosum62)

| | Swiss-Prot # | | | | |
|---|---|---|---|---|---|
| | Q9SDQ5 | P52884 | O04834 | O24110 | Q01474 |
| Protein name | SMALL GTP-BINDING PROTEIN SAR1BNT | GTP-BINDING PROTEIN SAR2 | GTP-BINDING PROTEIN SAR1A | SMALL GTP-BINDING PROTEIN | GTP-BINDING PROTEIN SAR1B |

TABLE 2-continued

Degree of amino acid identity and similarity of PpGBP-1 and other homologous proteins (Pairwise comparison program was used: gap penalty: 10; gap extension penalty: 0.1; score matrix: blosum62)

| | Swiss-Prot # | | | | |
|---|---|---|---|---|---|
| | Q9SDQ5 | P52884 | O04834 | O24110 | Q01474 |
| Species | Nicotiana tabacum (Common tobacco) | Lycopersicon esculentum (Tomato) | Arabidopsis thaliana (Mouse-ear cress) | Nicotiana plumbaginifolia (Leadwort-leaved tobacco) | Arabidopsis thaliana (Mouse-ear cress) |
| Identity % | 84% | 84% | 83% | 83% | 82% |
| Similarity % | 94% | 93% | 93% | 93% | 92% |

TABLE 3

Degree of amino acid identity and similarity of PpGBP-2 and other homologous proteins (Pairwise comparison program was used: gap penalty: 10; gap extention penalty: 0.1; score matrix: blosum62)

| | Swiss-Prot # | | | | |
|---|---|---|---|---|---|
| | P25387 | O24076 | Q9SXS0 | Q9SXR9 | Q40403 |
| Protein name | GUANINE NUCLEOTIDE-BINDING PROTEIN BETA SUBUNIT-LIKE PROTEIN | GUANINE NUCLEOTIDE-BINDING PROTEIN BETA SUBUNIT-LIKE PROTEIN | LEARCA2 PROTEIN | LEARCA1 PROTEIN | G PROTEIN BETA-SUBUNIT-LIKE PROTEIN |
| Species | Chlamydomonas reinhardtii | Medicago sativa (Alfalfa) | Lycopersicon esculentum (Tomato) | Lycopersicon esculentum (Tomato) | Nicotiana plumbaginifolia (Leadwort-leaved tobacco) |
| Identity % | 83% | 74% | 74% | 73% | 72% |
| Similarity % | 91% | 85% | 84% | 84% | 83% |

TABLE 4

Degree of amino acid identity and similarity of PpGBP-3 and other homologous proteins (Pairwise comparison program was used: gap penalty: 10; gap extension penalty: 0.1; score matrix: blosum62)

| | Swiss-Prot # | | | | |
|---|---|---|---|---|---|
| | Q9XER8 | Q40214 | O24461 | Q40526 | Q40213 |
| Protein name | RAS-RELATED PROTEIN RAB7 | RAB7D | RAS-RELATED PROTEIN RAB7 | SR1 NT-RAB7A | RAB7C |
| Species | Gossypium hirsutum (Upland cotton) | Lotus japonicus | Prunus armeniaca (Apricot) | Nicotiana tabacum (Common tobacco) | Lotus japonicus |
| Identity % | 87% | 87% | 87% | 85% | 85% |
| Similarity % | 94% | 93% | 93% | 92% | 90% |

TABLE 5

Degree of amino acid identity and similarity of PpGBP-4 and other homologous protein
(Pairwise comparison program was used: gap penalty: 10; gap extention penalty: 0.1;
score matrix: blosum62)

| | Swiss-Prot # | | | | |
|---|---|---|---|---|---|
| | Q9SE81 | Q9SMB6 | Q39118 | Q9M362 | O80499 |
| Protein name | DYNAMIN-LIKE PROTEIN 5 | PHRAGMO PLASTIN | GTP-BINDING PROTEIN (DYNAMIN-LIKE PROTEIN) | DYNAMIN-LIKE PROTEIN | DYNAMIN-LIKE PROTEIN PHRAGMO PLASTIN 12 |
| Species | Arabidopsis thaliana (Mouse-ear cress) | Nicotiana tabacum (Common tobacco) | Arabidopsis thaliana (Mouse-ear cress) | Arabidopsis thaliana (Mouse-ear cress) | Arabidopsis thaliana (Mouse-ear cress) |
| Identity % | 77% | 74% | 72% | 68% | 70% |
| Similarity % | 87% | 86% | 86% | 82% | 84% |

TABLE 6

Degree of amino acid identity and similarity of PpGBP-5 and other homologous proteins
(Pairwise comparison program was used: gap penalty: 10; gap extension penalty: 0.1; score
matrix: blosum62)

| | Swiss-Prot # | | | | |
|---|---|---|---|---|---|
| | O04150 | O64739 | Q9LUZ8 | P92985 | O04149 |
| Protein name | ATRANBP1B PROTEIN | ATRANBP1B PROTEIN | SIMILARITY TO SMALL GTPASE RAN BINDING PROTEIN 1 | RAN BINDING PROTEIN 1 HOMOLOG | ATRANBP1A PROTEIN |
| Species | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) | Arabidopsis thaliana (Mouse-ear cress) |
| Identity % | 46% | 46% | 39% | 44% | 44% |
| Similarity % | 58% | 58% | 52% | 57% | 56% |

Example 6

Cloning of the Full-Length *Physcomitrella patens* cDNA Encoding for GBP-1, GBP-2, GBP-3, GBP-4 and GBP-5

To isolate full-length PpGBP-2 (SEQ ID NO:7) PCR was performed as described below under Full-length Amplification using the original ESTs described in Example 5 as template since they were full-length (see Table 7 for primers). To isolate the clones encoding for PpGBP-1 (SEQ ID NO:6), PpGBP-3 (SEQ ID NO:8), PpGBP-4 (SEQ ID NO:9) and PpGBP-5 (SEQ ID NO:10) from *Physcomitrella patens*, cDNA libraries were created with SMART RACE cDNA Amplification kit (Clontech Laboratories) following manufacturer's instructions. Total RNA isolated as described in Example 3 was used as the template. The cultures were treated prior to RNA isolation as follows: Salt Stress: 2, 6, 12, 24, 48 h with 1-M NaCl-supplemented medium; Cold Stress: 4 C for the same time points as for salt; Drought Stress: cultures were incubated on dry filter paper for the same time points above. RNA was then pulled and used for isolation.

5' RACE Protocol

The EST sequences PpGBP-1 (SEQ ID NO:1), PpGBP-3 (SEQ ID NO:3), PpGBP-4 (SEQ ID NO:4), PpGBP-5 (SEQ ID NO:5), identified from the database search as described in Example 5 were used to design oligos for RACE (see Table 7). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions.

The sequences obtained from the RACE reactions contained the 5' end of the full-length coding regions of for PpGBP-1, PpGBP-3, PpGBP-4 and PpGBP-5 and were used to design oligos for full-length cloning of the respective genes (see below under "Full-length Amplification).

Full-Length Amplification

Full-length clones corresponding to PpGBP-2 (SEQ ID NO:7) were obtained by performing polymerase chain reaction (PCR) with gene-specific primers (see Table 7) and the original EST as the template. The conditions for the reaction were standard conditions with PWO DNA polymerase (Roche). PCR was performed according to standard conditions and to manufacture's protocols (Sambrook et al. 1989. Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C. and 1.5 minutes at 72° C. This was followed by twenty five cycles of one minute at 94° C., one minute at 65° C. and 1.5 minutes at 72° C. Full-length clones for PpGBP-1 (SEQ ID NO:6), PpGBP-3 (SEQ ID NO:8), PpGBP-4 (SEQ ID NO:9), PpGBP-5 (SEQ ID NO:10) were isolated by repeating the RACE method but using the gene-specific primers as given in Table 7.

The amplified fragments were then extracted from agarose gel with a QIAquick Gel Extraction Kit (Qiagen) and ligated into the TOPO pCR 2.1 vector (Invitrogen) following manufacture's instructions. Recombinant vectors were transformed into Top10 cells (Invitrogen) using standard conditions (Sambrook et al. 1989. Molecular Cloning, A Laboratory Manual. 2nd Edition. Cold Spring Harbor Laboratory Press. Cold Spring Harbor, N.Y.). Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3ml of liquid LB containing 100 µg/ml ampicillin and grown overnight at 37° C. Plasmid DNA was extracted using the QIAprep Spin Miniprep Kit (Qiagen) following manufacture's instructions. Analyses of subsequent clones and restriction mapping was performed according to standard molecular biology techniques (Sambrook et al. 1989 Molecular Cloning, A Laboratory Manual. 2nd Edition. Cold Spring Harbor Laboratory Press. Cold Spring Harbor, N.Y.).

TABLE 7

Scheme and primers used for cloning of full-length clones

| Gene | Sites in the final product | Isolation Method | Primers Race | Primer Full-length PCR |
|---|---|---|---|---|
| PpGBP-1 | XmaI/HpaI | 5' RACE and RT-PCR for Full-length clone | (SEQ ID NO: 19) TGCCAGCATT GTCGAGACCC AGAAA | RC586 (SEQ ID NO: 20) ATCCCGGGTCCG TAGATACCAAGG CTGGT RC587 (SEQ ID NO: 21) GCGTTAACTCGT CGCTCTTAAACA CCGAGCTAAG |
| PpGBP-2 | XmaI/SacI | PCR of original EST clone | N/A | RC403 (SEQ ID NO: 22) ATCCCGGGCCTC TCTTGCTCATCCC CAATGGCTG RC404 (SEQ ID NO: 23) GCGAGCTCGAGG CACTAATCAGAG AACGCCGTA |
| PpGBP-3 | XmaI/SacI | 5' RACE and RT-PCR for Full-length clone | (SEQ ID NO: 24) CACAACTGCC CTGGCTCCAA AATCA | RC497 (SEQ ID NO: 25) ATCCCGGGCAGG AGATTGGAGAAT CAGTCTGC RC498 (SEQ ID NO: 26) GCGAGCTCGACC CTGGCATTTCC ATCGCAGCAA |
| PpGBP-4 | XmaI/SacI | 5' RACE and RT-PCR for Full-length clone | (SEQ ID NO: 27) TACTGCATCC ACTACTGCCT CCGCT | RC568 (SEQ ID NO: 28) ATCCCGGGCACG CCTCCACCCTCTT GGGTCACA RC569 (SEQ ID NO: 29) GCGAGCTCCTGG GAGTTGAGGGCT TGGATGTAA |
| PpGBP-5 | XmaI/SacI | 5' RACE and RT-PCR for Full-length clone | (SEQ ID NO: 30) TGTCCTCCTC CTCGCCAGCC TTGGT | RC646 (SEQ ID NO: 31) ATCCCGGGCGTC CACCCTCAACCA GATTGGTGC RC647 (SEQ ID NO: 32) GCGAGCTCGCAA CTGGCGTACTTA TTAACACTA |

Example 7

Engineering Stress-Tolerant *Arabidopsis* Plants by Over-Expressing the Genes GBP-1, GBP-2, GBP-3, GBP-4 and GBP-5

Binary Vector Construction: pBPSSC022

The plasmid construct pACGH101 was digested with PstI (Roche) and FseI (NEB) according to manufacturers' instructions. The fragment was purified by agarose gel and extracted via the Qiaex II DNA Extraction kit (Qiagen). This resulted in a vector fragment with the *Arabidopsis* Actin2 promoter with internal intron and the OCS3 terminator. Primers for PCR amplification of the NPTII gene were designed as follows:

5'NPT-Pst: (SEQ ID NO:33)
GCG-CTG-CAG-ATT-TCA-TTT-GGA-GAG-GAC-ACG

3'NPT-Fse: (SEQ ID NO:34)
CGC-GGC-CGG-CCT-CAG-AAG-AAC-TCG-TCA-AGA-AGG-CG

The 0.9 kilobase NPTII gene was amplified via PCR from pCambia 2301 plasmid DNA [94° C. 60 sec, {94° C. 60 sec, 61° C. (−0.1° C. per cycle) 60 sec, 72° C. 2 min}×25 cycles, 72° C. 10 min on Biometra T-Gradient machine], and purified via the Qiaquick PCR Extraction kit (Qiagen) as per manufacturer's instructions. The PCR DNA was then subcloned into the pCR-BluntII TOPO vector (Invitrogen) pursuant to the manufacturer's instructions (NPT-Topo construct). These ligations were transformed into Top10 cells (Invitrogen) and grown on LB plates with 50 ug/ml kanamycin sulfate overnight at 37° C. Colonies were then used to inoculate 2 ml LB media with 50 ug/ml kanamycin sulfate and grown overnight at 37° C. Plasmid DNA was recovered using the Qiaprep Spin Miniprep kit (Qiagen) and sequenced in both the 5' and 3' directions using standard conditions. Subsequent analysis of the sequence data using VectorNTI software revealed no PCR errors present in the NPTII gene sequence.

The NPT-Topo construct was then digested with PstI (Roche) and FseI (NEB) according to manufacturers' instructions. The 0.9 kilobase fragment was purified on agarose gel and extracted by Qiaex II DNA Extraction kit (Qiagen). The Pst/Fse insert fragment from NPT-Topo and the Pst/Fse vector fragment from pACGH101 were then ligated together using T4 DNA Ligase (Roche) following manufacturer's instructions. The ligation was then transformed into Top10 cells (Invitrogen) under standard conditions, creating pBPSsc019 construct. Colonies were selected on LB plates with 50 µg/ml kanamycin sulfate and grown overnight at 37° C. These colonies were then used to inoculate 2 ml LB media with 50 µg/ml kanamycin sulfate and grown overnight at 37° C. Plasmid DNA was recovered using the Qiaprep Spin Miniprep kit (Qiagen) following the manufacturer's instructions.

The pBPSSC019 construct was digested with KpnI and BsaI (Roche) according to manufacturer's instructions. The fragment was purified via agarose gel and then extracted via the Qiaex II DNA Extraction kit (Qiagen) as per its instructions, resulting in a 3 kilobase Act-NPT cassette, which included the *Arabidopsis* Actin2 promoter with internal intron, the NPTII gene and the OCS3 terminator.

The pBPSJH001 vector was digested with SpeI and ApaI (Roche) and blunt-end filled with Klenow enzyme and 0.1 mM dNTPs (Roche) according to manufacture's instructions. This produced a 10.1 kilobase vector fragment minus the Gentamycin cassette, which was recircularized by self-ligating with T4 DNA Ligase (Roche), and transformed into Top10 cells (Invitrogen) via standard conditions. Transformed cells were selected for on LB agar containing 50 µg/ml kanamycin sulfate and grown overnight at 37° C. Colonies were then used to inoculate 2 ml of liquid LB containing 50 µg/ml kanamycin sulfate and grown overnight at 37° C. Plasmid DNA was extracted using the QIAprep Spin Miniprep Kit (Qiagen) following manufacture's instructions. The recircularized plasmid was then digested with KpnI (Roche) and extracted from agarose gel via the Qiaex II DNA Extraction kit (Qiagen) as per manufacturers' instructions.

The Act-NPT Kpn-cut insert and the Kpn-cut pBPSJH001 recircularized vector were then ligated together using T4 DNA Ligase (Roche) and transformed into Top10 cells (Invitrogen) as per manufacturers' instructions. The resulting construct, pBPSsc022, now contained the Super Promoter, the GUS gene, the NOS terminator, and the Act-NPT cassette. Transformed cells were selected for on LB agar containing 50 µg/ml kanamycin sulfate and grown overnight at 37° C. Colonies were then used to inoculate 2 ml of liquid LB containing 50 µg/ml kanamycin sulfate and grown overnight at 37° C. Plasmid DNA was extracted using the QIAprep Spin Miniprep Kit (Qiagen) following manufacturer's instructions. After confirmation of ligation success via restriction digests, pBPSsc022 plasmid DNA was further propagated and recovered using the Plasmid Midiprep Kit (Qiagen) following the manufacturer's instructions.

Subcloning of GBP-1, GBP-2, GBP-3, GBP-4 and GBP-5 into the Binary Vector

The fragments containing the different *Physcomitrella patens* transcription factors were subcloned from the recombinant PCR2.1 TOPO vectors by double digestion with restriction enzymes (see Table 8) according to manufacturer's instructions. The subsequence fragment was excised from agarose gel with a QIAquick Gel Extraction Kit (QIAgen) according to manufacture's instructions and ligated into the binary vectors pBPSsc022, cleaved with the appropriate enzymes (see Table 8) and dephosphorylated prior to ligation. The resulting recombinant pBPSsc022 contained the corresponding GTP-binding protein nucleic acid in the sense orientation under the constitutive super promoter.

TABLE 8

Listed are the names of the various constructs of the *Physcomitrella patens* transcription factors used for plant transformation

| Gene | Enzymes used to generate gene fragment | Enzymes used to restrict pBPSJH001 | Binary Vector Construct |
|---|---|---|---|
| PpGBP-1 | XmaI/HpaI | XmaI/Ecl136 | pBPSLVM162 |
| PpGBP-2 | XmaI/SacI | XmaI/SacI | pBPSJYW004 |
| PpGBP-3 | XmaI/SacI | XmaI/SacI | pBPSJYW001 |
| PpGBP-4 | XmaI/SacI | XmaI/SacI | pBPSLVM180 |
| PpGBP-5 | XmaI/SacI | XmaI/SacI | pBPSJYW006 |

*Agrabacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold 1993, Acad. Sci. Paris. 316:1194–1199; Bent et al. 1994, Science 265:1856–1860).

Screening of Transformed Plants

T1 seeds were sterilized according to standard protocols (Xiong et al. 1999, Plant Molecular Biology Reporter 17: 159–170). Seeds were plated on ½ Murashige and Skoog media (MS) (Sigma-Aldrich) pH 5.7 with KOH, 0.6% agar and supplemented with 1% sucrose, 0.5 g/L 2-[N-Morpholino]ethansulfonic acid (MES) (Sigma-Aldrich), 50 µg/ml kanamycin (Sigma-Aldrich), 500 µg/ml carbenicillan (Sigma-Aldrich) and 2 µg/ml benomyl (Sigma-Aldrich). Seeds on plates were vernalized for four days at 4° C. The seeds were germinated in a climatic chamber at an air temperature of 22° C. and light intensity of 40 micromol $s^{-1}m^{-2}$ (white light; Philips TL 65W/25 fluorescent tube) and 16 hours light and 8 hours dark day length cycle. Transformed seedlings were selected after 14 days and transferred to ½ MS media pH 5.7 with KOH 0.6% agar plates supplemented with 0.6% agar, 1% sucrose, 0.5 g/L MES (Sigma-Aldrich), and 2 µg/ml benomyl (Sigma-Aldrich) and allowed to recover for five-seven days.

Drought Tolerance Screening

T1 seedlings were transferred to dry, sterile filter paper in a petri dish and allowed to desiccate for two hours at 80% RH (relative humidity) in a Percival Growth CU3615, micromol $s^{-1}m^{-2}$ (white light; Philips TL 65W/25 fluorescent tube). The RH was then decreased to 60% and the seedlings were desiccated further for eight hours. Seedlings were then removed and placed on ½ MS 0.6% agar plates supplemented with 2 µg/ml benomyl (Sigma-Aldrich) and 0.5 g/L MES ((Sigma-Aldrich) and scored after five days.

Under drought stress conditions, PpGBP-1 over-expressing *Arabidopsis thaliana* plants showed an 45% (9 survivors from 20 stressed plants) survival rate to the stress screening; PpGBP-2, 84% (76 survivors from 90 stressed plants); PpGBP-3, 44% (4 survivors from 9 stressed plants); PpGBP-4, 82% (97 survivors from 116 stressed plants); plants); whereas the untransformed control had a 28% (16 survivors from 57 stressed plants) survival rate (see Table 9). It is noteworthy that the analyses of these transgenic lines were performed with T1 plants, and therefore, the results will be better when a homozygous, strong expresser is found.

TABLE 9

Summary of the drought stress tests

Drought Stress Test

| Gene Name | Number of survivors | Total number of plants | Percentage of survivors |
|---|---|---|---|
| PpGBP-1 | 9 | 20 | 45% |
| PpGBP-2 | 76 | 90 | 84% |
| PpGBP-3 | 4 | 9 | 44% |
| PpGBP-4 | 97 | 119 | 82% |
| Control | 16 | 57 | 28% |

Freezing Tolerance Screening

Seedlings were moved to petri dishes containing ½ MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C. decreasing −1° C. per hour. The seedlings were then incubated at −5.0° C. for 24 hours and then allowed to thaw at 5° C. for 12 hours. The water was poured off and the seedlings were scored after 5 days.

Under freezing stress conditions, PpGBP-1 over-expressing *Arabidopsis thaliana* plants showed an 60% (15 survivors from 25 stressed plants) survival rate to the stress screening; PpGBP-2, 75% (44 survivors from 59 stressed plants); PpGBP-3, 80% (8 survivors from 10 stressed plants); PpGBP-4, 87% (34 survivors from 39 stressed plants); PpGBP-5 75% (6 survivors from 8 stressed plants); whereas the untransformed control a 28% (16 survivors from 57 stressed plants) survival rate (see Table 10). It is noteworthy that the analyses of these transgenic lines were performed with T1 plants, and therefore, the results will be better when a homozygous, strong expresser is found.

TABLE 10

Summary of the freezing stress tests

Freezing Stress Test

| Gene Name | Number of survivors | Total number of plants | Percentage of survivors |
|---|---|---|---|
| PpGBP-1 | 15 | 25 | 60% |
| PpGBP-2 | 44 | 59 | 75% |
| PpGBP-3 | 8 | 10 | 80% |
| PpGBP-4 | 34 | 39 | 87% |
| PpGBP-5 | 6 | 8 | 75% |
| Control | 1 | 48 | 2% |

Salt Tolerance Screening

Seedlings were transferred to filter paper soaked in ½ MS and placed on ½ MS 0.6% agar supplemented with 2 µg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 µg/ml benomyl. The seedlings were scored after 5 days.

The transgenic plants are screened for their improved salt tolerance demonstrating that transgene expression confers salt tolerance.

Example 8

Detection of the GBP-1, GBP-2, GBP-3, GBP-4 and GBP-5 Transgenes in the Transgenic *Arabidopsis* Lines One leaf from a wild type and a transgenic *Arabidopsis* plant was homogenized in 250 µl Hexadecyltrimethyl ammonium bromide (CTAB) buffer (2% CTAB, 1.4 M NaCl, 8 mM EDTA and 20 mM Tris pH 8.0) and 1 µl β-mercaptoethanol. The samples were incubated at 60–65° C. for 30 minutes and 250 µl of Chloroform was then added to each sample. The samples were vortexed for 3 minutes and centrifuged for 5 minutes at 18,000×g. The supernatant was taken from each sample and 150 µl isopropanol was added. The samples were incubated at room temperature for 15 minutes, and centrifuged for 10 minutes at 18,000×g. Each pellet was washed with 70% ethanol, dried, and resuspended in 20 µl TE. 4 µl of above suspension was used in a 20 µl PCR reaction using Taq DNA polymerase (Roche Molecular Biochemicals) according to the manufacturer's instructions. Binary vector plasmid with each gene cloned in was used as positive control, and the wild type C24 genomic DNA was used as negative control in the PCR reactions. 10 µl PCR reaction was analyzed on 0.8% agarose/ethidium bromide gel. The PCR program used was as follows: 30 cycles of 1 minute at 94 C, 1 minute at 62 C and 4 minutes at 70 C, followed by 10 minutes at 72 C.

The 5' primer was as follows: 5'GCTGACACGC-CAAGCCTCGCTAGTC3' (SEQ ID NO:35). The gene-specific primers and the size of the amplified bands (Gene Product Size) are listed below:

PpGBP-1:
Primer: RC587: GCGTTAACTCGTCGCTCTTAAACAC-CGAGCTAAG
Gene Product: 700 bp (SEQ ID NO:36).

PpGBP-2:
Primer: RC404: GCGAGCTCGAGGCACTAATCA-GAGAACGCCGTA
Gene Product: 1000 bp (SEQ ID NO:37)

PpGBP-3:
Primer: RC498: GCGAGCTCGACCCTGGCATTTC-CCATCGCAGCAA
Gene Product: 700 bp (SEQ ID NO:38)

PpGBP-4:
Primer: RC569: GCGAGCTCCTGGGAGTTGAGGGCT-TGGATGTAA
Gene Product: 2100 bp (SEQ ID NO:39)

PpGBP-5:
Primer: RC647:GCGAGCTCGCAACTGGCGTACTTAT-TAACACTA
Gene Product: 900 bp (SEQ ID NO:40)

The transgenes were successfully amplified from the T1 transgenic lines, but not from the wild type C24. This result indicates that the T1 transgenic plants contain at least one copy of the transgenes. There was no indication of existence of either identical or very similar genes in the untransformed *Arabidopsis* thaliana control which could be amplified by this method.

Example 9

Detection of the GBP-1, GBP-2, GBP-3, GBP-4 and GBP-5Transgene mRNA in Transgenic *Arabidopsis* Lines Transgene expression was detected using RT-PCR. Total RNA was isolated from stress-treated plants using a procedure adapted from (Verwoerd et al., 1989 NAR 17:2362). Leaf samples (50–100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding 1/10$^{th}$ volume 3M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 µl DEPC treated water. To remove contaminating DNA from the samples, each was treated with RNase-free DNase (Roche) according to the manufacturer's recommendations. cDNA was synthesized from total RNA using the 1$^{st}$ Strand cDNA synthesis kit (Boehringer Mannheim) following manufacturer's recommendations.

PCR amplification of a gene-specific fragment from the synthesized cDNA was performed using Taq DNA polymerase (Roche) and gene-specific primers (see Table 4 for primers) in the following reaction: 1×PCR buffer, 1.5 mM MgCl$_2$, 0.2 µM each primer, 0.2 µM dNTPs, 1 unit polymerase, 5 µl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad). Expression of the transgenes was detected in the T1 transgenic line. These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 7.

TABLE 11

Primers used for the amplification of respective transgene mRNA in PCR using RNA isolated from transgenic *Arabidopsis thaliana* plants as template

| Gene | 5' primer | 3' primer |
| --- | --- | --- |
| PpGBP-1 | RC586: | RC587: |
|  | (SEQ ID NO:41) | (SEQ ID NO:42) |
|  | ATCCCGGGTCCGTAGA | GCGTTAACTCGTCGCTC |
|  | TACCAAGGCTGGT | TTAAACACCGAGCTAA |
|  |  | G |
| PpGBP-2 | RC403: | RC404: |
|  | (SEQ ID NO:43) | (SEQ ID NO:44) |
|  | ATCCCGGGCCTCTCTTG | GCGAGCTCGAGGCACT |
|  | CTCATCCCCAATGGCT | AATCAGAGAACGCCGT |
|  | G | A |
| PpGBP-3 | RC497: | RC498: |
|  | (SEQ ID NO:45) | (SEQ ID NO:46) |
|  | ATCCCGGGCAGGAGAT | GCGAGCTCGACCCTGG |
|  | TGGAGAATCAGTCTGC | CATTTCCCATCGCAGC |
|  |  | AA |
| PpGBP-4 | RC1227: | RC1228: |
|  | (SEQ ID NO:47) | (SEQ ID NO:48) |
|  | GGCACACAGGAGTACG | CGCTCTCTGCGTCTTGC |
|  | CAGAGTTTC | TGCTATCATG |
| PpGBP-5 | RC646: | RC647: |
|  | (SEQ ID NO:49) | (SEQ ID NO:50) |
|  | ATCCCGGGCGTCCACC | GCGAGCTCGCAACTGG |
|  | CTCAACCAGATTGGTG | CGTACTTATTAACACTA |
|  | C |  |

Example 10

Engineering Stress-Tolerant Soybean Plants by Over-Expressing the GBP-1, GBP-2, GBP-3, GBP-4 and GBP-5 Genes The constructs pBPSLVM162, pBPSJYW004, pBPSJYW001, pBPSLVM180 and pBPSJYW006 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacterial culture is pelleted at 7000 rpm for 7 minutes at room temperature, and resuspended in MS (Murashige and Skoog, 1962) medium supplemented with 100 µM acetosyringone. Bacterial cultures are incubated in this pre-induction medium for 2 hours at room temperature before use. The axes of soybean zygotic seed embryos at approximately 15% moisture content are imbibed for 2 hours at room temperature with the pre-induced *Agrabacterium* suspension culture. The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the agrobacteria. The liquid medium is used to moisten the sterile filter paper. The embryos are incubated for 4 weeks at 25° C., under 150 µmol m$^{-2}$sec$^{-1}$ and 12 hours photoperiod. Once the seedlings produced roots, they are transferred to sterile metromix soil. The medium of the in vitro plants is washed off before the plants are transferred to soil. The plants are kept under a plastic cover for 1 week to favor the acclimatization process. Then the plants are transferred to a growth room where they are incubated at 25° C., under 150 µmol m$^{-2}$sec$^{-1}$ light intensity and 12 hours photoperiod for about 80 days.

The transgenic plants are then screened for their improved drought, salt and/or cold tolerance according to the screening method described in Example 7 to demonstrate that transgene expression confers stress tolerance.

Example 11

Engineering Stress-Tolerant Rapeseed/Canola Plants by Over-Expressing the GBP-1, GBP-2, GBP-3, GBP-4 and GBP-5 Genes The constructs pBPSLVM162, pBPSJYW004, pBPSJYW001, pBPSLVM180 and pBPSJYW006 are used to transform rapeseed/canola as described below.

The method of plant transformation described herein is also applicable to Brassica and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approx. 85% of its water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7 demonstrating that transgene expression confers drought tolerance.

Example 12

Engineering Stress-Tolerant Corn Plants by Over-Expressing the GBP-1, GBP-2, GBP-3, GBP-4 and GBP-5 Genes The constructs pBPSLVM162, pBPSJYW004, pBPSJYW001, pBPSLVM180 and pBPSJYW006 are used to transform corn as described below.

Transformation of maize (*Zea Mays L.*) is performed with the method described by Ishida et al. 1996 Nature Biotech. 14745–50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved drought, salt and/or cold tolerance according to the screening method described in Example 7 demonstrating that transgene expression confers stress tolerance.

Example 13

Engineering Stress-Tolerant Wheat Plants by Over-Expressing the GBP-1, GBP-2, GBP-3, GBP-4 and GBP-5 Genes The constructs pBPSLVM162, pBPSJYW004, pBPSJYW001, pBPSLVM180 and pBPSJYW006 are used to transform wheat as described below.

Transformation of wheat is performed with the method described by Ishida et al. 1996 Nature Biotech. 14745–50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 demonstrating that transgene expression confers drought tolerance.

Example 14

Identification of Homologous and Heterologous Genes

Gene sequences can be used to identify homologous or heterologous genes from cDNA or genomic libraries.

Homologous genes (e. g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e. g. UV cross linking. Hybridization is carried out at high stringency conditions. In aqueous solution hybridization and washing is performed at an ionic strength of 1 M NaCl and a temperature of 68° C. Hybridization probes are generated by e. g. radioactive ($^{32}P$) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10–20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide Hybridization Solution:
6×SSC
0.01 M sodium phosphate
1 mM EDTA (pH 8)
0.5% SDS
100 µg/ml denatured salmon sperm DNA
0.1% nonfat dried milk During hybridization, temperature is lowered stepwise to 5–10° C. below the estimated oligonucleotide Tm or down to room temperature followed by washing steps and autoradiography. Washing is performed with low stringency such as 3 washing steps using 4×SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 15

Identification of Homologous Genes by Screening Expression Libraries with Antibodies c-DNA clones can be used to produce recombinant protein for example in *E. coli* (e. g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994 BioTechniques 17:257–262. The antibody can than be used to screen expression cDNA libraries to identify homologous or heterologous genes via an immunological screening (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons).

Example 16

In Vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella*, p. 2277–2294, ASM: Washington.) Such strains are well known to those skilled in the art. The use of such strains is illustrated, for example, in Greener, A. and Callahan, M. (1994) *Strategies* 7: 32–34. Transfer of mutated DNA molecules into plants is preferably done after selection and testing in microorganisms. Transgenic plants are generated according to various examples within the exemplification of this document.

Example 17

In Vitro Analysis of the Function of *Physcomitrella* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβ1, M., eds. (1983–1986) Methods of Enzymatic Analysis, $3^{rd}$ ed., vol. I–XII, Verlag Chemie: Weinheim; and Ullmann's Encyclopedia of Industrial Chemistry (1987) vol. A9, Enzymes. VCH: Weinheim, p. 352–363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) *EMBO J.* 14: 3895–3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B. Pores, Channels and Transporters, in Biomembranes, Molecular Structure and Function, pp. 85-137, 199–234 and 270–322, Springer: Heidelberg (1989).

Example 18

Purification of the Desired Product from Transformed Organisms

Recovery of the desired product from plant material (i.e., *Physcomitrella patents* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonication. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supemate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 *Appl. Environ. Microbiol.* 60:133–140; Malakhova et al., 1996 *Biotekhnologiya* 11:27–32; and Schmidt et al., 1998 *Bioprocess Engineer.* 19:67–70. Ulmann's Encyclopedia of Industrial Chemistry, (1996) vol. A27, VCH: Weinheim, p. 89–90, p. 521–540, p. 540–547, p. 559–566, 575–581 and p. 581–587; Michal, G. (1999) Bioch Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

APPENDIX

Partial cDNA Sequence of Pp GBP-1 from *Physcomitrella patens*     (SEQ ID NO:1)

```
TTTTTTTTTTTTGGGGGAACAATATTTGGAAGATACACTTTACTTCATAA

TTCGGAAGGTCAAAAACTGTCTAGAAAACCAAAACGTTCCCGATTACATG

CACATCCAGCAAAACTCTGATCGTTATCGTCGCTCTTAAACACCGAGCTA

AGTTCCTCTTTCACAGGAAAACAATCACTTGATGTACTGGGTCATCCACT

TGAAACCTTCACCGTACCCCATTTTGCGCACAATACTGCACATGAAAACC

TCAATGGGCCGAATGTTGCTATCTCCCAGGTTCACCGTTCCTTTACCAGT

GGTCATGGTCAACCCAAGTGTGAACCGCAACTCGTCTTCAGAAGAAGCGT

ACGGGATATCAATCTTGTTTCCCAGGACGAGCACAGGAACTTGGGACAGA

GAATCGTCGGAGAGAAGAGAATCGAGCTCTTTCTTTGACTCAGCAAATCT

CTCCCTGTCTACTGCGTCGACGAGATACACTATAGCATCCACCTTAGCAT

AGTAGTCCCTCCACACGCGTCGAGCGATTGTGTGGCCACCCAGATCGAAT

GCTTTGAACTTCACTCTGTTGATACTCAACTCCTCTGACGTTGGATACTG

CGTTGGTTGATGTTGCCCCAGTTTCTCATCCTTGAGCATGTGCAGAAGAG

TAGTCTTGCCAGCATTGTCGAGACCCAGAAACAGGATTTTGGCCTCCTTC

TGCCACAGCCCTATGCTCGCAAGAAAGCCGTAAAACCAATCTACAAGAAA

CATGGTACCAGCCTTGGTATCTACGGACCCGCCCCAATTTTCCACGACCT

CGTGC
```

Partial cDNA Sequence of PpGBP-2 from *Physcomitrella patens*     (SEQ ID NO:2)

```
GCACCAGGCGCCGCCTGCCTCAGCTCTTAGTTCTCCGAATTTGACACTTG

TTTCGTTTGCTTCCTTCTTTTTTTATTTTTTTATTTTCTTCTTAGTCTT

CTTCCTCTCTTGCTCATCCCCAATGGCTGAGACTTTAGTGCTGCGCGGGA
```

APPENDIX-continued

```
CTTTGAAGGGTCATTCCAACTGGGTGACCGCCATCGCCTGCCCTCTCGAC

AACCCTGACCTCATCCTCTCGTCGTCTCGCGACAAGAGCATCATCGTCTG

GACCCTCACCCGCGAGGAGGGCAACTATGGTGTCGCCCGCCGTAGGCTGA

CCGGGCACGCTCACTTCGTGCAGGATGTGGTGATCTCCTCCGACGGACAG

TTCGCCCTGTCGGGGTCGTGGGACGGGACCTTGCGTTTGTGGGATTTGAA

CACCGGAACTACCACCCGGCGGTTCATCGGTCACACCAAGGATGTGCTCA

GCGTGGCTTTCTCCGTTGATAACAGACAGATTGTGTCGGGATCCCGCGAC

AAGACAATCAAGCTGTGGAACACTCTTGGTGAGTGCAAGTACACCATCCA

GGACGTCGATGCCCACACTGGGTGGGTGAGCTGCGTCCGATTCTCCCCTG

TGACTGCTAACCCTATCATTGTGTCCGGTGGGTGGGACAAGGTTGTCAAG

GTGTGGAACCTGACCAACTGC
```

Partial cDNA Sequence of PpGBP-3 from *Physcomitrella patens* (SEQ ID NO:3)

```
GTATTCCCCCGTTGTTTCAAGCTTTTGCAAACCTGAATCACATCACGTT

GAGTCTTCTGCTGAGTCTCAAAGTAGGGGATCCCTCCTTTCCTGGCACAC

CATGCTTTGCCTTCTTCTCGGAGACCACTCGACTATTGCCACCATCCACG

TCCACTTTATGTTCCAAGTACTACAAAGGGGAAGTTCTCCTGATCGGATG

GGCTTGCCTGAATCAGAAACTCGTCCCTCCAGTTGTCAAGGTTATCAAAA

GACTTCATAACATTCACATCGTAGACAAGAACACAACATCTGCACCACGA

TAAAAGGCGACTCCAAGACTCTGAAACCGCTCTTGCCCAGCTGTATCCCA

AATCTGCATCGTAACAAGTCTGTCTTCAACCTGCACTTCCTTAGTTAGAA

AGTCTGCCCCAATAGTGGCCTTATATTGATTGCTGAATTTCTTATTAACA

TACTGATTCATCAAAGAAGTCTTTCCAACCCCGCTATCACCGAGGATGAT

AACTTTCAACAACGTCCTCTTGCGGGCCGACATCGCAGACTGATTCTCCA

ATCTCCTGCTTCCAATTCTTAACCCTCACAACTGCCCTGGCTCCAAAATC

ACGCCTTCCTTCACGACTCCCTCCCCGGTCCCAAGCAGAGCTTCTCGATG

AAAATTGTTCTTCGAAAACCGAGATCCGCGGCTGTAGTGCATCAAATTCT

ACAAGGAAGAGTGCGTTCTGGTGCCGAGGAATCGAGCGTACACTGGTGC
```

Partial cDNA Sequence of PpGBP-4 from *Physcomitrella patens* (SEQ ID NO:4)

```
CGGCACCAGAAAATATACGCGGTGTTCGACAATCAACTGCCAGCTGCTTT

GAAGAAGCTTCCGTTCGACAAGCATCTGTCTGGGCAGAATGTGCGAAGGA

TTGTTTCGGAGGCTGATGGTTACCAGCCCCATCTTATAGCTCCGGAGCAA

GGTTACAGGCGGCTAATTGAAAGTTCGCTGCAATTTTTCAGGGGCCCAGC

GGAGGCAGTAGTGGATGCAGTAAGTCACTCTGTTGCAACGATAAATGAAC

AGTAACGTTTCTAGATTTTCACGAATTCAATTTTTCTCCATCAAGGATAT

TTTCTAGTCACGACATTCTGCATACTTACCAGTAGCACAGGGTTCGGCTG

ATTCGTGATTGTGTGACAACCCAGGTGCATTTCATTCTTAGGGACCTGGT

GCGAAAATCGATCGGAGAGTGTTCGGTAAGGGTCTGAGACTTTGGAATTT

CCTTGCCTGTAAGAACGTGCTGGGTTACCAGCGGAACCTGTCACTTGTGA

CCACCAAGAGTGCTAGCTATATCTTTCTAGCTTATGTTAATTGGTTTAAT

GTTTTTAGTACCTCACTGACTTAAACCGAACTTGGAAGCGAGAATAGGAA

TGATGTGCTTGATGTCAACCTTCATTCTCACAGGAACTGAAGAGATTTCC
```

APPENDIX-continued

```
ATCACTCCAAGCGGAGATGGTCAAGCAGCCATTGAGTCGTTAGAGAGGAT

GAAGATGAGAGCAGAAGACCCTTTGAGGCGGGGACATGGAATCACCTACC

TGACGGGCAATTTTCCGAAGCTGCGAAAATGNAAGGTGAACCGCGCGCAG

TAAGACGTACGGTAC
```

Partial cDNA Sequence of PpGBP-5 from *Physcomitrella patens* (SEQ ID NO:5)
```
GCACGAGTGCTTCTGTAGCTCCCGATTCACCTGCCTTGCATAGATCGTCG

TCCACCCTCAACCAGATTGGTGCACAATGGCCGCAGACGACGAGAAGCAA

GCACGGGAGGTGGAGGAGACAACCGGATCGGAAGCTCCTGCGGAAGGAGCTGA

TGAGCCTACCAAGGCTGGCGAGGAGGAGGACACAGGTGCTCAAATCGCGCCTAT

CGTAACATTACAGGAAGTTGCTGTTAGCACTGGCGAAGAGGAT

GAAGACGTGCTGATTGATATGAAAGCTAAGCTTTACCGATTTGACAAGGA

AGGAACCCAGTGGAAAGAGCGGGGCGTTGGCCAAGTTAAGATATTAGAGC

ATAAGACTACCAGAAAGGTCCGATTGCTCATGCGACAAAATCGGACCCTG

AAGATCTGTGCTAATCACATGGTTACGGCAGCTACTCAACTGCAAGAGCA

CGCTGGTAGTGATAAGTCATGGATATGGCATGCGCGAGAC
```

Full-length cDNA Sequence of PpGBP-1 from *Physcomitrella patens* (SEQ ID NO:6)
```
ATCCCGGGTCCGTAGATACCAAGGCTGGTACCATGTTTCTTGTAGATTGGTTTTA

CGGCTTTCTTGCGAGCATAGGGCTGTGGCAGAAGGAGGCCAAAATCCTGTTTCTG

GGTCTCGACAATGCTGGCAAGACTACTCTTCTGCACATGCTCAAGGATGAGAAA

CTGGGGCAACATCAACCAACGCAGTATCCAACGTCAGAGGAGTTGAGTATCAAC

AGAGTGAAGTTCAAAGCATTCGATCTGGGTGGCCACACAATCGCTCGACGCGTG

TGGAGGGACTACTATGCTAAGGTGGATGCTATAGTGTATCTCGTCGACGGAGTAG

ACAGGGAGAGATTTGCTGAGTCAAAGAAAGAGCTCGATTCTCTTCTCTCCGACG

ATTCTCTGTCCCAAGTTCCTGTGCTCGTCCTGGGAAACAAGATTGATATCCCGTA

CGCTTCTTCTGAAGACGAGTTGCGGTTCACACTTGGGTTGACCATGACCACTGGT

AAAGGAACGGTGAACCTGGGAGATAGCAACATTCGGCCCATTGAGGTTTTCATG

TGCAGTATTGTGCGCAAAATGGGGTACGGTGAAGGTTTCAAGTGGATGACCCAG

TACATCAAGTGATTGTTTTCCTGTGAAAGAGGAACTTAGCTCGGTGTTTAAGAGC

GACGAGTTAACGC
```

Full-length cDNA Sequence of PpGBP-2 from *Physcomitrella patens* (SEQ ID NO:7)
```
ATCCCGGGCCTCTCTTGCTCATCCCCAATGGCTGAGACTTTAGTGCTGCGCGGGA

CTTTGAAGGGTCATTCCAACTGGGTGACCGCCATCGCCTGCCCTCTCGACAACCC

TGACCTCATCCTCTCGTCGTCTCGCGACAAGAGCATCATCGTCTGGACCCTCACC

CGCGAGGAGGGCAACTATGGTGTCGCCCGCCGTAGGCTGACCGGGCACGCTCAC

TTCGTGCAGGATGTGGTGATCTCCTCCGACGGACAGTTCGCCCTGTCGGGTCGT

GGGACGGGACCTTGCGTTTGTGGGATTTGAACACCGGAACTACCACCCGGCGGT

TCATCGGTCACACCAAGGATGTGCTCAGCGTGGCTTTCTCCGTTGATAACAGACA

GATTGTGTCGGGATCCCGCGACAAGACAATCAAGCTGTGGAACACTCTTGGTGA

GTGCAAGTACACCATCCAGGACGTCGATGCCCACACTGGGTGGGTGAGCTGCGT

CCGATTCTCCCCTGTGACTGCTAACCCTATCATTGTGTCCGGTGGGTGGGACAAG

GTTGTCAAGGTGTGGAACCTGACCAACTGCAAGATTCGCTCCAACTTGGTTGGCC
```

APPENDIX-continued

```
ACACCGGATATGTCAACACAGTAACTGTATCCCCTGATGGTTCGTTGTGCGCCAG

CGGAGGTAAGGATGGAGTCGCCATGTTGTGGGATTTGTCTGAGGGCAAGAGGCT

GTACTCACTGGACGCCGGTGATATCATCCACTCCCTTTGCTTTAGCCCCAACAGA

TACTGGTTGTGTGCCGCCACCCAATCCTGCATCAAGATCTGGGACTTGGAGAGCA

AGAGCATTGTCGATGAGTTGCGCCCCGAGTTCACTTTCGTCAGTAAGAAGGCCCA

GATTCCTTACTGCGTCAGCTTGAACTGGAGCGCTGACGGGAGCACTCTTTTCAGT

GGTTACACTGATGGCCACATTAGGGTGTGGGCCGTCGGAAGGGCTTAAGCGTCT

TCTCATTTACGGGGTCGCAATGCGGAAGTACGGCGTTCTCTGATTAGTGCCTCGA

GCTCGC
```

Full-length cDNA Sequence of PpGBP-3 from *Physcomitrella patens*    (SEQ ID NO:8)
```
ATCCCGGGCAGGAGATTGGAGAATCAGTCTGCGATGTCGGCCCGCAAGAGGACG

TTGTTGAAAGTTATCATCCTCGGTGATAGCGGGGTTGGAAAGACTTCTTTGATGA

ATCAGTATGTTAATAAGAAATTCAGCAATCAATATAAGGCCACTATTGGGCAG

ACTTTCTAACTAAGGAAGTGCAGGTTGAAGACAGACTTGTTACGATGCAGATTTG

GGATACAGCTGGGCAAGAGCGGTTTCAGAGTCTTGGAGTCGCCTTTTATCGTGGT

GCAGATTGTTGTGTTCTTGTCTACGATGTGAATGTTATGAAGTCTTTTGATAACCT

TGACAACTGGAGGGACGAGTTTCTGATTCAGGCAAGCCCATCCGATCAGGAGAA

CTTCCCCTTTGTAGTACTTGGAAATAAAGTGGACGTGGATGGTGGCAATAGTCGA

GTGGTCTCCGAGAAGAAGGCCAAAGCATGGTGTGCAGCGAAAGGAGGCATCCCC

TACTTTGAGACATCAGCCAAGGAAGACTTCAACGTGGATGCTGCATTCCAGTGTA

TTGCCAAGAACGCATTGAAGAACGAGACGGAGGAGGAAATTTACCTGCCTGATA

CGATCGACGTGAACGCCAGCAGGCCACAGAAAACTTCCGGATGCGAGTGTTAAG

AGTAGCGGAGTTGCTGCGATGGGAAATGCCAGGTCGAGCTCGC
```

Full-length cDNA Sequence of PpGBP-4 from *Physcomitrella patens*    (SEQ ID NO:9)
```
ATCCCGGGCACGCCTCCACCCTCTTGGGTCACATCTCTTTCTTCTCTGGTGGGCGT

CGCACTTCTGCAACCGATCGCCGGAAGCCTAGATACCGACATTGGCGGTACCAG

GCTTGCGGGACTTGGGCGTAACGAATACTTGTAAATCCAAGGGGAGATTGCAAG

ATGGATAATTTGATTGGGCTTGTGAATAGGATTCAGAGGGCTTGCACTGCCCTCG

GTGACCATGGAGGCGAAGGTGCAGTTGCAAGTCTCTGGGAGGCCTTGCCTTCGG

TTGCTGTCGTTGGTGGGCAGAGTTCGGGAAAGTCTTCAGTGCTGGAAAGTATCGT

TGGACGTGATTTTCTCCCTCGGGGTTCTGGTATCGTTACTAGGCGTCCGTTGGTTT

TGCAACTGCACAAAACTGATGAAGGCACACAGGAGTACGCAGAGTTTCTCCACA

TGCCCAAAAAGCGGTTTACTGACTTTGCTGCTGTAAGGAAGGAGATCTCAGACG

AGACGGACCGAATGACTGGACGGGGCAAGGGAATTTCGGTTGTGCCAATTCAGC

TTAGCGTTTATTCCCCCAATGTTGTGAATTTGACTCTCATCGATCTTCCGGGACTT

ACAAAAATTGCTGTTGATGGCCAATCCGACAGCATCGTGCAAGACATTGAGAAC

ATGGTCCGGTCATATATTGAGAAGCAAAATTCTATCATTCTTGCCGTGTCTCCAG

CGAATCAAGATATCGCCACTTCAGATGCTATGAAGATTGCTAGAGAAGTGGATC

CTACTGGAGAGAGGACTTTTGGGGTCCTTACCAAGTTGGATCTGATGGACAAGG

GGACAAATGCCCTTGATGTCCTTGAAGGACGCTCCTACCGTTTACAACATCCGTG

GGTAGGAGTTGTGAATCGTTCCCAGCAGGACATCAACAAGGAAGTGAACATGAT
```

APPENDIX-continued

```
AGCAGCAAGACGCAGAGAGCGAGAATACTTTGCAACCAGTCAAGATTACGGTCA
CCTGGCCAGCAAGATGGGTTCTGAATATTTGGGGAAAGTGCTCTCCAAGCATTTG
GAAGCCGTGATCAAGTCCCGTATTCCTAGCATCCAGGCTATGATTAACAAAAGT
ATTGACGAGATCGAGATGGAGCTGAATCAGATCGGCCGGCCTCTTGCAAATGAT
GCAGGGGCTCAGCTGTACACTATCCTGGAACTTTGTCGGGCCTTCGATCGAATCT
TCAAGGACCATCTGGATGGAGCACGCCCCGGTGGTGATAAAATATACGCGGTGT
TCGACAATCAACTGCCAGCTGCTTTGAAGAAGCTTCCGTTCGACAAGCATCTGTC
TGGGCAGAATGTGCGAAGGATTGTTTCGGAGGCTGATGGTTACCAGCCCCATCTT
ATAGCTCCGGAGCAAGGTTACAGGCGGCTAATTGAAAGTTCGCTGCAATTTTTCA
AGGGCCCAGCGGAGGCAGTAGTGGATGCAGTGCATTTCATTCTTAGGGACCTGG
TGCGAAAATCGATCGGAGAGTGTTCGGAACTGAAGAGATTTCCATCACTCCAAG
CGGAGATTGCTCAAGCAGCCATTGAGTCGTTAGAGAGGATGAGAGATGAGAGCA
AGAAGACCACTTTGAGGCTGGTGGACATGGAATCCAGCTACCTGACCGTGGACT
TTTTCCGAAAGCTGCCGCAAGAGATTGAGAAGGGTGGAAACGCTGCTGCCGCAG
CTAACGACCGTTACACGGATAACCACTTGCGGCGCATTGGTTCCAATGTGGCAGC
GTACGTTGGCATGGTTTGCGATCAGCTGAGGAACTCTTTGCCCAAAGCTGCTGTC
CACTGTCAAGTTCGAGAAGCGAAGAGGTCATTGATGGACCACTTTTACACTCAA
ATAGGCAAGCGGGAGGGAAAGCAATTGTCAGCGATGCTGGATGAGGACCCTGCT
TTGATGGAACGGAGAGTTCAGCTGTCAAAGAGACTGGAGCTTTACAAACAAGCC
AGGGACGAGATTGATTCTGTTGCCTGGAAGTAGTTGGGGGGTCGTACTTAATTTA
TACCTATTTCATTACTGAATGTTGCATTTATTCATAGCAGCTCTTTTCCCTTGGAG
AACGATAATTACAGTTACATCCAAGCCCTCAACTCCCAGGAGCTCGC
```

Full-length cDNA Sequence of PpGBP-5 from *Physcomitrella patens*     (SEQ ID NO:10)
```
ATCCCGGGCGTCCACCCTCAACCAGATTGGTGCACAATGGCCGCAGACGACGAG
AAGCAAGCACGGGAGGTGGAGGAGACAACCGGATCGGAAGCTCCTGCGGAAGG
AGCTGATGAGCCTACCAAGGCTGGCGAGGAGGAGGACACAGGTGCTCAAATCGC
GCCTATCGTAACATTACAGGAAGTTGCTGTTAGCACTGGCGAAGAGGATGAAGA
CGTGCTGATTGATATGAAAGCTAAGCTTTACCGATTTGACAAGGAAGGAACCCA
GTGGAAAGAGCGGGGCGTTGGCCAAGTTAAGATATTAGAGCATAAGACTACCAG
AAAGGTCCGATTGCTCATGCGACAAAATCGGACCCTGAAGATCTGTGCTAATCA
CATGGTTACGGCAGCTACTCAACTGCAAGAGCACGCTGGTAGTGATAAGTCATG
GATATGGCATGCGCGAGACTATTCAGACGGCGAGTTAAAGGAGGAGCTTTTCTG
CATGCGATTTGGCAGTGTTGAAAGCGCCCAAAAGTTTAAAGATGTTTATGAGGCT
GCCCAGGAGAAGGTGTCTAGCAAGACAGAGGAGAAGGACGAGGAGGCTGATGC
GACTGCAGACCTTTTACAAAATTTGAAAGTGGAACCAAAAACTGATAAGGTCGA
TGTTCCTGAGGAAACGAATACTGGAACCAAAGCAGCGTAGATTGGACAGTATGG
GTGTGATCAACATGTGCTTGGGTCGTTGGAAGGTAGTTATACGTGGCACTAAACT
GGTTTCGAGTGTTGATGTTTTTAAACCCTCGTCCAGGGTCGGAATTTGGAATGCT
TCTCCTGAAGTGAAAAAAGTTAATCGTGTAAACCTTTATTAGTGTTAATAAGTAC
GCCAGTTGCGAGCTCGC
```

APPENDIX-continued

Deduced Amino Acid Sequence of PpGBP-1 from *Physcomitrella patens* (SEQ ID NO:11)
MFLVDWFYGFLASIGLWQKEAKILFLGLDNAGKTTLLHMLKDEKLGQHQPTQYPTS

EELSINRVKFKAFDLGGHTIARRVWRDYYAKVDAIVYLVDAVDRERFAESKKELDSL

LSDDSLSQVPVLVLGNKIDIPYASSEDELRFTLGLTMTTGKGTVNLGDSNIRPIEVFMC

SIVRKMGYGEGFKWMTQYIK*

Deduced Amino Acid Sequence of PpGBP-2 from *Physcomitrella patens* (SEQ ID NO:12)
MAETLVLRGTLKGHSNWVTAIACPLDNPDLILSSSRDKSIIVWTLTREEGNYGVARRR

LTGHAHFVQDVVISSDGQFALSGSWDGTLRLWDLNTGTTTRRFIGHTKDVLSVAFSV

DNRQIVSGSRDKTIKLWNTLGECKYTIQDVDAHTGWVSCVRFSPVTANPIIVSGGWD

KVVKVWNLTNCKIRSNLVGHTGYVNTVTVSPDGSLCASGGKDGVAMLWDLSEGKR

LYSLDAGDIIHSLCFSPNRYWLCAATQSCIKIWDLESKSIVDELRPEFTFVSKKAQIPYC

VSLNWSADGSTLFSGYTDGHIRVWAVGRA*

Deduced Amino Acid Sequence of PpGBP-3 from *Physcomitrella patens* SEQ ID NO:13)
MSARKRTLLKVIILGDSGVGKTSLMNQYVNKKFSNQYKATIGADFLTKEVQVEDRL

VTMQIWDTAGQERFQSLGVAFYRGADCCVLVYDVNVMKSFDNLDNWRDEFLIQAS

PSDQENFPFVVLGNKVDVDGGNSRVVSEKKAKAWCAAKGGIPYFETSAKEDFNVD

AAFQCIAKNALKNETEEEIYLPDTIDVNASRPQKTSGCEC*

Deduced Amino Acid Sequence of PpGBP-4 from *Physcomitrella patens* (SEQ ID NO:14)
MDNLIGLVNRIQRACTALGDHGGEGAVASLWEALPSVAVVGGQSSGKSSVLESIVG

RDFLPRGSGIVTRRPLVLQLHKTDEGTQEYAEFLHMPKKRFTDFAAVRKEISDETDR

MTGRGKGISVVPIQLSVYSPNVVNLTLIDLPGLTKIAVDGQSDSIVQDIENMVRSYIEK

QNSIILAVSPANQDIATSDAMKIAREVDPTGERTFGVLTKLDLMDKGTNALDVLEGR

SYRLQHPWVGVVNRSQQDINKEVNMIAARRREREYFATSQDYGHLASKMGSEYLG

KVLSKHLEAVIKSRIPSIQAMINKSIDEIEMELNQIGRPLANDAGAQLYTILELCRAFDR

IFKDHLDGARPGGDKIYAVFDNQLPAALKKLPFDKHLSGQNVRRIVSEADGYQPHLI

APEQGYRRLIESSLQFFKGPAEAVVDAVHFILRDLVRKSIGECSELKRFPSLQAEIAQA

AIESLERMRDESKKTTLRLVDMESSYLTVDFFRKLPQEIEKGGNAAAAANDRYTDNH

LRRIGSNVAAYVGMVCDQLRNSLPKAAVHCQVREAKRSLMDHFYTQIGKREGKQLS

AMLDEDPALMERRVQLSKRLELYKQARDEIDSVAWK*

Deduced Amino Acid Sequence of PpGBP-5 from *Physcomitrella patens* (SEQ ID NO:15)
MAADDEKQAREVEETTGSEAPAEGADEPTKAGEEEDTGAQIAPIVTLQEVAVSTGEE

DEDVLIDMKAKLYRFDKEGTQWKERGVGQVKILEHKTTRKVRLLMRQNRTLKICAN

HMVTAATQLQEHAGSDKSWIWHARDYSDGELKEELFCMRFGSVESAQKFKDVYEA

AQEKVSSKTEEKDEEADATADLLQNLKVEPKTDKVDVPEETNTGTKAA

We claim:

1. A transgenic plant cell transformed with a polynucleotide selected from the group consisting of:
   a) a polynucleotide having nucleotides 1 to 667 of SEQ ID NO:6; and
   b) a polynucleotide encoding a polypeptide having amino acids 1 to 192 of SEQ ID NO:11.

2. The plant cell of claim 1, wherein the polynucleotide has the sequence as defined in SEQ ID NO:6.

3. The plant cell of claim 1, wherein the polynucleotide encodes the polypeptide having the sequence as defined in SEQ ID NO:11.

4. A transgenic plant comprising the plant cell of claim 1.

5. The plant of claim 4, wherein the plant is a monocot.

6. The plant of claim 4, wherein the plant is a dicot.

7. The plant of claim 4, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and a forage crop plant.

8. A plant seed comprising a transgene selected from the group consisting of:
   a) a polynucleotide having nucleotides 1 to 667 of SEQ ID NO:6; and
   b) a polynucleotide encoding a polypeptide having amino acids 1 to 192 of SEQ ID NO:11,
and wherein the seed is true breeding for increased tolerance to drought or low temperature.

9. An isolated polynucleotide selected from the group consisting of:
   a) a polynucleotide having nucleotides 1 to 667 of SEQ ID NO:6; and
   b) a polynucleotide encoding a polypeptide having amino acids 1 to 192 of SEQ ID NO:11.

10. The polynucleotide of claim 9, having the sequence as defined in SEQ ID NO:6.

11. The polynucleotide of claim 9, encoding the polypeptide having the sequence as defined in SEQ ID NO:11.

12. A method of producing a transgenic plant comprising a polynucleotide encoding a polypeptide, wherein expression of the polypeptide in the plant results in the plant having increased tolerance to an environmental stress as compared to a wild type variety of the plant, the method comprising the steps of,
   a) transforming a plant cell with an expression vector comprising the polynucleotide; and
   b) generating from the plant cell a transgenic plant that expresses the polypeptide,
wherein the polynucleotide is selected from the group consisting of:
   a) a polynucleotide having nucleotides 1 to 667 of SEQ ID NO:6; and
   b) a polynucleotide encoding a polypeptide having amino acids 1 to 192 of SEQ ID NO:11,
and wherein the environmental stress is selected from the group consisting of drought and low temperature.

13. The method of claim 12, wherein the polynucleotide has the sequence as defined in SEQ ID NO:6.

14. The method of claim 12, wherein the polynucleotide encodes the polypeptide having the sequence as defined in SEQ ID NO:11.

* * * * *